US012797820B2

(12) United States Patent
Qiao et al.

(10) Patent No.: US 12,797,820 B2
(45) Date of Patent: Nov. 17, 2026

(54) ADSORBENT FOR TRIMETHYLBENZENE-BASED COMPOUNDS AND PREPARATION METHOD THEREOF, AND SEPARATION METHOD AND SEPARATION APPARATUS FOR TRIMETHYLBENZENE-BASED COMPOUNDS

(71) Applicants: CHINA PETROLEUM & CHEMICAL CORPORATION, Beijing (CN); SINOPEC RESEARCH INSTITUTE OF PETROLEUM PROCESSING CO., LTD., Beijing (CN)

(72) Inventors: Xiaofei Qiao, Beijing (CN); Weiqiang Liu, Beijing (CN); Jianfeng Ma, Beijing (CN); Yanqiang Yang, Beijing (CN); Hongchao Wang, Beijing (CN); Yusi Liu, Beijing (CN); Lunxi Li, Beijing (CN); Zhichao Jiang, Beijing (CN)

(73) Assignees: CHINA PETROLEUM & CHEMICAL CORPORATION, Beijing (CN); SINOPEC RESEARCH INSTITUTE OF PETROLEUM PROCESSING CO., LTD., Beijing (CN)

( * ) Notice: Subject to any disclaimer, the term of this patent is extended or adjusted under 35 U.S.C. 154(b) by 251 days.

(21) Appl. No.: 18/704,727

(22) PCT Filed: Oct. 25, 2022

(86) PCT No.: PCT/CN2022/127260

§ 371 (c)(1),
(2) Date: Apr. 25, 2024

(87) PCT Pub. No.: WO2023/072035

PCT Pub. Date: May 4, 2023

(65) Prior Publication Data

US 2025/0325955 A1 Oct. 23, 2025

(30) Foreign Application Priority Data

Oct. 25, 2021 (CN) ......................... 202111238515.1
Oct. 25, 2021 (CN) ......................... 202111238672.2

(51) Int. Cl.
*B01J 20/18* (2006.01)
*B01D 3/14* (2006.01)
(Continued)

(52) U.S. Cl.
CPC ............ *B01J 20/186* (2013.01); *B01D 3/141* (2013.01); *B01D 3/143* (2013.01); *B01D 15/14* (2013.01);
(Continued)

(58) Field of Classification Search
CPC .................... B01D 3/141; B01J 20/186; B01J 20/28004; B01J 20/28011; B01J 20/28016;
(Continued)

(56) References Cited

U.S. PATENT DOCUMENTS 3,558,730 A 1/1971 Neuzil
3,997,620 A 12/1976 Neuzil
(Continued)

FOREIGN PATENT DOCUMENTS

CN 101704706 A 5/2010
CN 102746094 A 10/2012
(Continued)

OTHER PUBLICATIONS

English-language machine translation of CN 110508240 A (Year: 2019).*

*Primary Examiner* — James C Goloboy
(74) *Attorney, Agent, or Firm* — NKL Law; Allen Xue

(57) ABSTRACT

An adsorbent for trimethylbenzene-based compounds, contains, relative to the total amount of X-type molecular sieve and matrix, 93-99 wt % of X-type molecular sieve and 1-7 wt % of matrix. The matrix is a substance after crystal transformation through in-situ crystallization of clay mineral, the adsorbent is modified with at least one bivalent cation selected from $Mg^{2+}$, $Ca^{2+}$, $Sr^{2+}$, $Fe^{2+}$, $Co^{2+}$, $Ni^{2+}$ and
(Continued)

$Zn^{2+}$ and optionally modified with at least one monovalent cation selected from $Li^+$, $Na^+$, $K^+$, $Rb^+$ and $Cs^+$. A method for preparing the adsorbent, a method of separating trimethylbenzene-based compounds by using the adsorbent, and an apparatus for separating trimethylbenzene-based compounds are provided.

10 Claims, 3 Drawing Sheets

(51) Int. Cl.

| | |
|---|---|
| ***B01D 15/14*** | (2006.01) |
| ***B01D 15/18*** | (2006.01) |
| ***B01D 15/20*** | (2006.01) |
| ***B01J 20/28*** | (2006.01) |
| ***B01J 20/284*** | (2006.01) |
| ***B01J 20/30*** | (2006.01) |
| ***B01J 20/34*** | (2006.01) |
| ***C07C 7/13*** | (2006.01) |

(52) U.S. Cl.
CPC ..... *B01D 15/1835* (2013.01); *B01D 15/1842* (2013.01); *B01D 15/185* (2013.01); *B01D 15/203* (2013.01); *B01J 20/28004* (2013.01); *B01J 20/28011* (2013.01); *B01J 20/28016* (2013.01); *B01J 20/28064* (2013.01); *B01J 20/284* (2013.01); *B01J 20/3007* (2013.01); *B01J 20/3028* (2013.01); *B01J 20/3078* (2013.01); *B01J 20/3085* (2013.01); *B01J 20/3408* (2013.01); *B01J 20/3475* (2013.01); *C07C 7/13* (2013.01)

(58) Field of Classification Search
CPC ................ B01J 20/28064; B01J 20/284; B01J 20/3007; B01J 20/3028; B01J 20/3078; B01J 20/3085; B01J 20/3408; B01J 20/3475; C07C 7/13
See application file for complete search history.

(56) References Cited

U.S. PATENT DOCUMENTS

| | | | | |
|---|---|---|---|---|
| 4,376,226 A * | 3/1983 | Rosenfeld | C07C 7/13 585/828 |
| 2014/0155674 A1* | 6/2014 | Wang | C07C 7/12 585/828 |

FOREIGN PATENT DOCUMENTS

| | | | | |
|---|---|---|---|---|
| CN | 105542835 A | 5/2016 | |
| CN | 110508240 A * | 11/2019 | B01J 20/041 |
| CN | 112642391 A | 4/2021 | |
| EP | 0165470 A2 * | 12/1985 | C07C 4/00 |
| EP | 1148025 A1 | 10/2001 | |
| JP | 2002226406 A | 8/2002 | |

* cited by examiner

ADSORBENT FOR TRIMETHYLBENZENE-BASED COMPOUNDS AND PREPARATION METHOD THEREOF, AND SEPARATION METHOD AND SEPARATION APPARATUS FOR TRIMETHYLBENZENE-BASED COMPOUNDS

TECHNICAL FIELD

The present invention refers to an adsorbent for trimethylbenzene-based compounds, a preparation method thereof, and a separation method and separation apparatus for applying the same for separation by adsorbing trimethylbenzene-based compounds as a whole. Specifically, the present invention relates to an adsorbent for separation by adsorbing high-purity 1,3,5-trimethylbenzene, 1,2,4-trimethylbenzene, 1,2,3-trimethylbenzene, and a separation method and separation apparatus for separation by adsorbing high-purity 1,3,5-trimethylbenzene, 1,2,4-trimethylbenzene, 1,2,3-trimethylbenzene.

BACKGROUND OF ART

C9+ heavy aromatic hydrocarbon is an important by-product of petrochemical and coal-coking plants. In recent years, the chemical industry has paid more and more attention to their comprehensive utilization. With the successive commissioning of many domestic integrated projects, the reforming unit production capacity will reach 190 million tons in 2022, and the reformed heavy aromatic hydrocarbon production capacity is expected to get more than 30 million tons. There are currently three ways to utilize heavy aromatic hydrocarbons: the first is as an oil blending component; the second is to increase the production of light aromatic hydrocarbons such as BTX (benzene-toluene-xylene mixture); the third is to produce high-boiling point solvent oil. The third utilization route has a higher degree of wasting resources and lower product added value.

On the one hand, heavy aromatic hydrocarbon resources are increasing and raw material prices are declining. In the past ten years, the price of heavy aromatic hydrocarbons has generally shown a downward trend. In 2021, the price of heavy aromatic hydrocarbons per ton has been reduced to 3,200 yuan. On the other hand, heavy aromatic hydrocarbon utilization apparatuses of most manufacturers currently involve reactions such as extraction, cryogenic crystallization and alkylation coupled with multiple distillation columns. Their products are relatively single, with low purity and yield, complex process flow, high investment cost, high operating energy consumption, low comprehensive extraction degree, and low product-added value. Therefore, the market urgently needs technological innovation to improve the resource utilization of heavy aromatic hydrocarbons, maximize the economic added value of heavy aromatic hydrocarbon products, and extend the industrial chain.

Three trimethylbenzenes, which account for almost half of the heavy aromatic hydrocarbons, have the highest proportion in the reformed heavy aromatic hydrocarbon. They are important fine chemical intermediates with high utilization value. 1,2,4-trimethylbenzene is currently obtained through multiple-column distillation or extraction distillation, but there are requirements for the composition of the raw materials, especially the requirements for the content of para-tert-butylbenzene are relatively strict. China is the largest producer and consumer of 1,2,4-trimethylbenzene, and its demand is increasing year by year. 1,2,4-trimethylbenzene can be used to produce phthalic anhydride, further produce environmentally friendly plasticizers, as well as trimethylhydroquinone, which is an intermediate in the production of vitamin E, or methylated to produce durene, further producing the most promising plastic of the 21st century-polyimide, which is widely used in fields such as aerospace, supersonic aircraft, atomic energy industry, and electromechanical industry. Currently, 1,3,5-trimethylbenzene is obtained through extraction distillation, alkylation, or isomerization, but each method has certain drawbacks. For example, extraction distillation has high energy consumption; alkylation consumes a large amount of propylene and the cost is high; and isomerization is susceptible to interference from other C9 components, and the product yield is only about 15%, 1,3,5-trimethylbenzene can be used to produce expensive antioxidants, dyes, and environmentally friendly herbicides. China is a large agricultural country, and the demand for environmentally friendly herbicides is also increasing year by year. Currently, 1,2,3-trimethylbenzene is commonly sold as a high boiling solvent oil, and its monomer can also be obtained through alkylation, extraction-precision distillation, precision distillation-cryogenic crystallization, and the like. However, due to the extremely difficult separation from the indan component, the entire separation process consumes high energy, with a purity of only 50 wt %-80 wt %, and poor economic efficiency. 1,2,3-trimethylbenzene can be used to produce musk tibetene, as a daily spice in cosmetics and daily chemical products, or to produce aniline dyes, alkyd resin, polyester resin and trimesic acid, or to react with benzoyl chloride and phenylacetyl chloride to produce pain killers, platelet anti-coagulants, thromboinhibitors and other drugs. However, due to the huge investment in its separation and purification, there is less industrial production in China.

The adsorption separation process has the characteristic of selectively adsorbing specific components, with a relatively simple process flow, fewer by-products, and less susceptibility to interference from other components. Compared to multiple distillation columns connected in series, the energy consumption is lower.

U.S. Pat. No. 3,558,730 disclosed a BaKX molecular sieve with significantly higher selectivity for paraxylene (PX) than BaX and KX. U.S. Pat. No. 3,997,620 found that compared with BaKX, after exchanging the X molecular sieve with Sr2+ and Ba2+, although paraxylene/metaxylene (PX/MX) and paraxylene/orthoxylene (PX/OX) decreased, however paraxylene/ethylbenzene (PX/EB) and paraxylene/para-diethylbenzene (PX/PDEB) significantly increased. CN1565718A uses small crystalline particle X molecular sieve with a crystal particle size of 0.1-0.4 micron as the active component of the adsorbent to improve its mass transfer performance and increase the adsorption capacity.

The configuration and electrostatic potential of three isomers of trimethylbenzene in the reformed heavy aromatic hydrocarbons have certain general characteristics. Therefore, by combining adsorption separation and distillation processes, the three isomers of trimethylbenzene can be separated from the heavy aromatic hydrocarbon simultaneously, and then monomer products can be obtained with high yield and high purity through conventional steps such as distillation. At present, most adsorbents using X-type molecular sieves as active components are used for the adsorption and separation of para aromatic hydrocarbons. However, there have been no reports on adsorbents that exhibit selectivity for all three trimethylbenzene isomers and possess both high bulk density and high compression strength.

SUMMARY OF THE INVENTION

To solve the above problems, the inventors of the present invention have conducted in-depth research and surprisingly found that by combining an X-type molecular sieve and a substance obtained after crystal transformation through in-situ crystallization of clay mineral, and through specific ion exchange modification, the obtained adsorbent has very high selectivity for trimethylbenzene-based compounds, and can be used to separate high-purity trimethylbenzene monomers from heavy aromatic hydrocarbons.

That is to say, the present invention provides the following technical solutions.

[1] An adsorbent for trimethylbenzene-based compounds, which is characterized in that, relative to the total amount of X-type molecular sieve and matrix, it comprises 93-99 wt % of X-type molecular sieve and 1-7 wt % of matrix, the matrix is a substance after crystal transformation through in-situ crystallization of clay mineral, the adsorbent is modified with at least one bivalent cation selected from $Mg^{2+}$, $Ca^{2+}$, $Sr^{2+}$, $Fe^{2+}$, $Co^{2+}$, $Ni^{2+}$ and $Zn^{2+}$ (preferably $Sr^{2+}$) and optionally modified with at least one monovalent cation selected from $Li^{+}$, $Na^{+}$, $K^{+}$, $Rb^{+}$ and $Cs^{+}$ (preferably $Li^{+}$).

[2] The adsorbent according to [1], characterized in that, the adsorbent has a water mass fraction of 1-10%, preferably 2-8%, more preferably 2.5-6.0%.

[3] The adsorbent according to [1] or [2], characterized in that, the adsorbent has a BET specific surface area of not less than 560 $m_2/g$, preferably not less than 590 $m^2/g$.

[4] The adsorbent according to any one of [1]-[3], characterized in that, the adsorbent has an exchange degree of bivalent cation of not less than 75%, preferably not less than 85%, more preferably not less than 93%.

[5] The adsorbent according to any one of [1]-[4], characterized in that, the adsorbent has a crushing rate at 130 N of 0.3%-1.0% (preferably 0.3%-0.6%), a bulk density of 0.40-0.95 $g/cm^3$ (preferably 0.75-0.78 $g/cm^3$).

[6] The adsorbent according to any one of [1]-[5], characterized in that, the X-type molecular sieve has a crystal particle size of 0.5-2.0 micron.

[7] The adsorbent according to any one of [1]-[6], characterized in that, the X-type molecular sieve has a molar ratio of silica to alumina of 2.0-2.6, preferably 2.0-2.4.

[8] The adsorbent according to any one of [1]-[7], characterized in that, the clay mineral is selected from non-metal clay minerals.

[9] The adsorbent according to any one of [1]-[8], characterized in that, the clay mineral is at least one of kaolin mineral, bentonite mineral, attapulgite mineral, sepiolite mineral, and illite mineral.

[10] The adsorbent according to [9], characterized in that, the kaolin mineral is at least one of kaolinite, dickite, nacrite, firestone and halloysite.

[11] The adsorbent according to [9], characterized in that, the bentonite mineral is at least one of activated clay, natural bleaching earth, and organo-bentonite.

[12]. A method for preparing the adsorbent for trimethylbenzene-based compounds according to any one of [1]-[11], characterized in that said method comprises the following steps:

(1) shaping into particles: mixing an X molecular sieve and a clay mineral at a mass ratio of 91-98:2-9, shaping into particles, optionally drying, and then calcining at 500 °C-680 °C;

(2) in-situ crystallization: treating calcined particles with an alkali solution and then drying to produce particles as the matrix, the concentration of hydroxide ions in the alkali solution is 0.2 mol/L-2.0 mol/L (preferably 0.2 mol/L-1.6 mol/L), (3) ion exchange: subjecting the particles as matrix obtained in step (2) to the cation exchange with an exchange solution of a compound containing at least one bivalent cation selected from $Mg^{2+}$, $Ca^{2+}$, $Sr^{2+}$, $Fe^{2+}$, $Co^{2+}$, $Ni^{2+}$ and $Zn^{2+}$ (preferably $Sr^{2+}$), and optionally a compound containing at least one monovalent cation selected from $Li^{+}$, $Na^{+}$, $K^{+}$, $Rb^{+}$ and $Cs^{+}$ (preferably $Li^{+}$), and then drying the ion-exchanged solid.

[13] The preparation method according to [12], characterized in that, after step (3), the method further comprises (4) activation step: activating the dried product of step (3), preferably at an activation temperature of 150 °C-260 °C, more preferably 180 °C-250 °C.

[14] The preparation method according to [12]or [13], characterized in that, the alkali solution is a solution of at least one of lithium hydroxide, potassium hydroxide, sodium hydroxide, and ammonium hydroxide, preferably a mixed solution of sodium hydroxide and potassium hydroxide, more preferably the molar ratio of K/(Na+K) in the alkali solution is 0-0.50 (preferably 0.15-0.40).

[15] The preparation method according to any one of [12]-[14], characterized in that, the liquid/solid ratio of the alkali solution to the calcined particles is 1.5 L/kg-5.0 L/kg.

[16] The preparation method according to any one of [12]-[15], characterized in that, in the step of in-situ crystallization, the crystallization temperature is 80 °C-100 °C.

[17] The preparation method according to any one of [12]-[16], characterized in that, in the step of in-situ crystallization, the particles as matrix obtained after drying have a particle size of 400 micron to 950 micron.

[18] The preparation method according to any one of [12]-[17], characterized in that, in the step of ion exchange, the compound containing at least one bivalent cation selected from $Mg^{2+}$, $Ca^{2+}$, $Sr^{2+}$, $Fe^{2+}$, $Co^{2+}$, $Ni^{2+}$ and $Zn^{2+}$ (preferably $Sr^{2+}$) is selected from at least one of nitrates and chlorides thereof, the compound containing at least one monovalent cation selected from $Li^{+}$, $Na^{+}$, $K^{+}$, $Rb^{+}$ and $Cs^{+}$ (preferably $Li^{+}$) is selected from at least one of nitrates, chlorides and carbonates thereof.

[19] The preparation method according to any one of [12]-[18], characterized in that, in the step of ion exchange, in the exchange solution, the concentration of the bivalent cation is not less than 0.15 mol/L, the volume ratio of the exchange solution to the particles is not less than 3.

[20] The preparation method according to any one of [12]-[19], characterized in that, in the step of ion exchange, the molar ratio of the bivalent cation to the monovalent cation in the exchange solution is not less than 3, preferably not less than 4.

[21] A method for separating trimethylbenzene-based compounds, which comprises the following steps:

adsorption separation: contacting a heavy aromatic hydrocarbon raw material containing trimethylbenzene-based compounds with the adsorbent according to any one of [1]-[11] or the adsorbent prepared with the preparation method according to any one of [12]-[20] to adsorb trimethylbenzene-based compounds, and then performing the separation to produce trimethylbenzene-based compounds.

[22] The separation method according to [21], characterized in that, the heavy aromatic hydrocarbon raw material is selected from reforming product, pyrolysis gasoline, naphtha, ethylbenzene-apparatus by-product or catalytically cracked gasoline, preferably a reformed heavy aromatic hydrocarbon fraction, more preferably a reformed heavy aromatic hydrocarbon fraction having a boiling point of 150 °C or higher.

[23] The separation method according to [22], characterized in that, the heavy aromatic hydrocarbon raw material is a reformed heavy aromatic hydrocarbon having a total mass fraction of trimethylbenzene-based compounds of 20% or higher.

[24] The separation method according to any one of [21]-[23], relative to the unit mass of adsorbent, the flow rate of the heavy aromatic hydrocarbon raw material is not less than 0.16 kg/(h·kg adsorbent), preferably not less than 0.20 kg/(h·kg adsorbent), more preferably not less than 0.23 kg/(h·kg adsorbent).

[25] The separation method according to any one of [21]-[24], characterized in that, trimethylbenzene-based compounds are separated from the adsorbent by using an alkylbenzene (preferably toluene) as desorbent.

[26] The separation method according to any one of [21]-[25], characterized in that, in the step of adsorption separation, a simulated moving bed apparatus is used, preferably, the simulated moving bed apparatus comprises multiple adsorption beds with loaded adsorbent, each bed has its material injection and withdrawing pipelines, materials that are withdrawn from and injected into the simulated moving bed apparatus divide adsorption beds therein into desorption zone, purification zone, adsorption zone and isolation zone, the adsorption beds between desorbent injection and extract withdrawing constitute the desorption zone, the adsorption beds between extract withdrawing and raw material injection constitute the purification zone, the adsorption beds between raw material injection and raffinate withdrawing constitute the adsorption zone, the adsorption beds between raffinate withdrawing and desorbent injection constitute the isolation zone.

[27] The separation method according to [26], characterized in that, during one step time, the withdrawing and injection order of each material in the material flowing direction of the simulated moving bed is desorbent, extract, raw material and raffinate.

[28] The separation method according to [26], characterized in that, the pressure of the simulated moving bed apparatus constitute is 0.5 MPa-1.2 MPa (preferably 0.6 MPa-1.0 MPa), the temperature is 120 °C-200 °C. (140 °C-180 °C).

[29] The separation method according to [26], characterized in that, the ratio of mass flow rates of the desorbent and the heavy aromatic hydrocarbon raw material injected into the simulated moving bed apparatus (desorbent/heavy aromatic hydrocarbon raw material) is not greater than 3.6, preferably not greater than 3.4, more preferably not greater than 3.2.

[30] The separation method according to [26], characterized in that, the simulated moving bed apparatus comprises an adsorption zone, a purification zone, a desorption zone and an isolation zone, and has a ratio of bed numbers of 29±10%:37±15%:21±5%:13±4%.

[31] The separation method according to [26], characterized in that, the simulated moving bed apparatus has one cycle period of 18-60 minutes, preferably 25-35 minutes.

[32] The separation method according to [26], characterized in that, each adsorption bed of the simulated moving bed is provided with a grid, which is equipped with material injection and withdrawing pipelines of said bed, two flushing liquor pipelines are set up in parallel with material injection and withdrawing pipelines of each adsorption bed; each pipeline is provided with an on-off valve, the extract is used as the flushing liquor, the flushing liquor from one flushing liquor pipeline is injected into a bed that is located one bed upstream the raw material injection bed, and the flushing liquor from the other flushing liquor pipeline is injected into a bed that is located 2-4 beds downstream the extract withdrawing position.

[33] The separation method according to [32], characterized in that, the grid of each adsorption bed is equipped with one withdrawing and injection pipeline, and multiple parallel on-off valves are set up on the pipeline to control materials to be withdrawn from and injected into the adsorbent beds.

[34] The separation method according to [32], characterized in that, the withdrawing and injection pipelines of each adsorbent bed are provided with 6-7 on-off valves.

[35] The separation method according to [32], characterized in that, each adsorption bed is provided with a pipeline for which the flushing liquor is used as the desorbent, the injection position of which is one bed upstream the extract withdrawing position.

[36] The separation method according to any one of [21]-[35], characterized in that, said method further comprises the following steps, distillation step: trimethylbenzene-based compounds obtained from the adsorption separation are subjected to distillation to produce 1,3,5-trimethylbenzene, 1,2,4-trimethylbenzene, and 1,2,3-trimethylbenzene respectively.

[37] The separation method according to [36], characterized in that, in the distillation step, an extract stream from the adsorption separation step is sent to a dividing wall column, 1,3,5-trimethylbenzene is produced from the top of the dividing wall column, 1,2,4-trimethylbenzene is produced from the side-line of the dividing wall column, 1,2,3-trimethylbenzene is produced from the bottom of the dividing wall column.

[38] The separation method according to [36], characterized in that, in the distillation step, an extract stream from the adsorption separation step is sent to the first distillation column, 1,3,5-trimethylbenzene is produced by separation from the column top of the first distillation column, the bottom product of the first distillation column is sent to a second distillation column, 1,2,4-trimethylbenzene is produced by separation from the column top of the second distillation column, 1,2,3-trimethylbenzene is produced from the column bottom of the second distillation column.

[39] The separation method according to [36],
characterized in that, in the distillation step, an extract stream from the adsorption separation step is sent to the first distillation column, 1,3,5-trimethylbenzene is produced by separation from the column top of the first distillation column, the bottom product of the first distillation column is sent to a second distillation column, 1,2,4-trimethylbenzene is produced by separation from the column top of the second distillation column, the bottom product of the second distillation column is sent to a third distillation column, 1,2,3-trimethylbenzene is produced by separation from the column top of the third distillation column, the bottom product is an aromatic solvent oil with high boiling point.

[40] The separation method according to [36],
characterized in that, in the distillation step, an extract stream from the adsorption separation step is sent to the first distillation column, 1,3,5-trimethylbenzene is produced by separation from the column top of the first distillation column, the column bottom stream is a mixture of 1,2,4-trimethylbenzene and 1,2,3-trimethylbenzene, 1,2,4-trimethylbenzene and 1,2,3-trimethylbenzene are further separated by using a crystallization process.

[41] The separation method according to [36],
characterized in that, in the distillation step, 1,2,3-trimethylbenzene can be separated from an extract stream from the adsorption separation step by using a crystallization process, a mixture stream of the residual 1,2,4-trimethylbenzene and 1,3,5-trimethylbenzene is sent to the first distillation column, 1,3,5-trimethylbenzene is produced by separation from the column top of the first distillation column, the column bottom stream is 1,2,4-trimethylbenzene.

[42] The separation method according to any one of [21]-[41],
characterized in that, trimethylbenzene-based compounds obtained from the adsorption separation step have a total purity of not less than 99 wt %.

[43] The separation method according to any one of [36]-[42],
characterized in that, 1,3,5-trimethylbenzene, 1,2,4-trimethylbenzene, and 1,2,3-trimethylbenzene obtained from the distillation step have purities of not less than 97.0 wt %, 98.0 wt % and 95.0 wt %, preferably not less than 98.5 wt %, 99.3 wt % and 97.0 wt % respectively.

[44] The separation method according to any one of [21]-[43],
characterized in that, said method further comprises an isomerization step, the isomerization step is between the adsorption separation and the distillation step, and trimethylbenzene-based compounds are subjected to the isomerization, or the isomerization step is after the distillation step, at least one of 1,3,5-trimethylbenzene, 1,2,4-trimethylbenzene, and 1,2,3-trimethylbenzene is subjected to the isomerization.

[45] The separation method according to any one of [44],
characterized in that, after one trimethylbenzene or a mixture of trimethylbenzenes is isomerized, the obtained mixture stream of trimethylbenzenes with a thermodynamic equilibrium concentration is returned to the adsorption separation step for separation.

[46] The separation method according to any one of [44],
characterized in that, in the distillation step, in the case of using two distillation columns, the stream sent to the isomerization unit is produced from the side-line of first distillation column,
or,
in the distillation step, in the case of using three distillation columns, the stream sent to the isomerization unit can be produced from the side-line of the first distillation column or the second distillation column.

[47] The separation method according to any one of [26]-[46],
characterized in that, said method further comprises:
raffinate separation step: a raffinate from the simulated moving bed apparatus is subjected to distillation to produce a desorbent and a heavy aromatic hydrocarbon component in which trimethylbenzene-based compounds have been separated by adsorption.

[48] An apparatus for separating trimethylbenzene-based compounds, which comprises the following units:
adsorption separation unit: having the adsorbent according to any one of [1]-[11] or the adsorbent prepared with the preparation method according to any one of [12]-[20], and used to adsorb and separate trimethylbenzene-based compounds from a heavy aromatic hydrocarbon raw material containing trimethylbenzene-based compounds to produce trimethylbenzene-based compounds.

[49] The separation apparatus according to [48],
characterized in that, the adsorption separation unit adopts a simulated moving bed, preferably, the simulated moving bed comprises multiple adsorption beds with loaded adsorbent, each bed has its material injection and withdrawing pipelines, materials that are withdrawn from and injected into the simulated moving bed apparatus divide adsorption beds therein into desorption zone, purification zone, adsorption zone and isolation zone, the adsorption beds between desorbent injection and extract withdrawing constitute the desorption zone, the adsorption beds between extract withdrawing and raw material injection constitute the purification zone, the adsorption beds between raw material injection and raffinate withdrawing constitute the adsorption zone, the adsorption beds between raffinate withdrawing and desorbent injection constitute the isolation zone.

[50] The separation apparatus according to [49],
characterized in that, the simulated moving bed apparatus comprises an adsorption zone, a purification zone, a desorption zone and an isolation zone, and has a ratio of bed numbers of 29±10%:37±15%:21±5%:13±4%.

[51] The separation apparatus according to [49],
characterized in that, each adsorption bed of the simulated moving bed is provided with a grid, which is equipped with material injection and withdrawing pipelines of said bed, two flushing liquor pipelines are set up in parallel with material injection and withdrawing pipelines of each adsorption bed; each pipeline is provided with an on-off valve, the extract is used as the flushing liquor, the flushing liquor from one flushing liquor pipeline is injected into a bed that is located one bed upstream the raw material injection bed, and the flushing liquor from the other flushing liquor pipeline is injected into a bed that is located 2-4 beds downstream the extract withdrawing position.

[52] The separation apparatus according to [49], characterized in that, the grid of each adsorption bed is equipped with one withdrawing and injection pipeline, and multiple parallel on-off valves are set up on the pipeline to control materials to be withdrawn from and injected into the adsorbent beds.

[53] The separation apparatus according to [49], characterized in that, the withdrawing and injection pipelines of each adsorbent bed are provided with 6-7 on-off valves.

[54] The separation apparatus according to [49], characterized in that, each adsorption bed is provided with a pipeline for which the flushing liquor is used as the desorbent, the injection position of which is one bed upstream the extract withdrawing position.

[55] The separation apparatus according to any one of [48]-[54], characterized in that, said apparatus further comprises: distillation unit: which is connected to the downstream of the adsorption separation unit, receives a stream containing trimethylbenzene-based compounds from the adsorption separation unit, and performs the distillation to produce 1,3,5-trimethylbenzene, 1,2,4-trimethylbenzene, and 1,2,3-trimethylbenzene respectively.

[56] The separation apparatus according to [55], characterized in that, the distillation unit comprises a dividing wall column, to which the extract stream from the adsorption separation step is introduced, the column top of the dividing wall column is provided with 1,3,5-trimethylbenzene discharge outlet, the side-line of the dividing wall column is provided with 1,2,4-trimethylbenzene discharge outlet, the column bottom of the dividing wall column is provided with 1,2,3-trimethylbenzene discharge outlet.

[57] The separation apparatus according to [55], characterized in that, the distillation unit comprises a first distillation column and a second distillation column successively connected in series, the column bottom of the first distillation column is connected to the second distillation column, the column top of the first distillation column is provided with a discharge outlet for 1,3,5-trimethylbenzene, the column top of the second distillation column is provided with a discharge outlet for 1,2,4-trimethylbenzene, the column bottom of the second distillation column is provided with a discharge outlet for 1,2,3-trimethylbenzene.

[58] The separation apparatus according to [55], characterized in that, the distillation unit comprises a first distillation column, a second distillation column and a third distillation column successively connected in series, the column bottom of the first distillation column is connected to the second distillation column, the column top of the first distillation column is provided with a discharge outlet for 1,3,5-trimethylbenzene, the column bottom of the second distillation column is connected to the third distillation column, the column top of the second distillation column is provided with a discharge outlet for 1,2,4-trimethylbenzene, the column top of the third distillation column is provided with a discharge outlet for 1,2,3-trimethylbenzene, the column bottom of the third distillation column is provided with a discharge outlet for aromatic solvent oil with high boiling point.

[59] The separation apparatus according to any one of [48]-[57], characterized in that, said apparatus further comprises: raffinate distillation unit: which is connected to the downstream of the adsorption separation unit, receives a stream containing the heavy aromatic hydrocarbon component in which trimethylbenzene-based compounds have been separated by adsorption from the adsorption separation unit, and in which the distillation is performed, to produce a heavy aromatic hydrocarbon component in which trimethylbenzene-based compounds have been separated by adsorption and a desorbent respectively.

[60] The separation apparatus according to any one of [48]-[59], characterized in that, the separation apparatus further comprises, isomerization unit, which is located between the adsorption separation unit and the distillation unit, and used to receive a stream containing trimethylbenzene-based compounds from the adsorption separation unit, and in which the isomerization is performed; or which is connected to the downstream of the distillation unit, used to receive at least one of 1,3,5-trimethylbenzene, 1,2,4-trimethylbenzene, and 1,2,3-trimethylbenzene from the distillation unit, and in which the isomerization is performed.

[61] The separation apparatus according to [60], characterized in that, in the case that the distillation unit has two distillation columns, the side-line of first distillation column is provided with an isomerization stream outlet, or, in the case that the distillation unit has three distillation columns, the side-line of the first distillation column or the second distillation column has an isomerization stream outlet.

[62] Use of the adsorbent according to any one of [1]-[11] or the adsorbent prepared with the preparation method according to any one of [12]-[20] for adsorbing trimethylbenzene-based compounds from heavy aromatic hydrocarbon raw material.

Technical Effect

The adsorbent of the present invention has high bulk density and high compression strength, and at the same time has excellent selectivity for three trimethylbenzenes, and is suitable for adsorbing and separating high-purity trimethylbenzene monomers from heavy aromatic hydrocarbons, thereby improving the resource utilization of heavy aromatic hydrocarbons and increasing the economic added value of heavy aromatic hydrocarbons.

According to the separation method of trimethylbenzene compounds of the present invention, high-purity trimethylbenzene monomers can be continuously separated from heavy aromatic hydrocarbons with high purity, high selectivity and high yield. Trimethylbenzene-based compounds obtained with the separation method of the present invention have a total purity of not less than 99 wt %. For trimethylbenzene-based compounds obtained through adsorption separation, 1,2,4-trimethylbenzene, 1,3,5-trimethylbenzene, and 1,2,3-trimethylbenzene monomers with high purities can be produced simultaneously through distillation process with high yield, relatively simple process, good product quality, and low energy consumption. The resource utilization efficiency can be improved, and the economic added value of heavy aromatic hydrocarbon products can be greatly increased, bringing considerable economic benefits to the enterprise.

DETAILED DESCRIPTION

Figure 1:
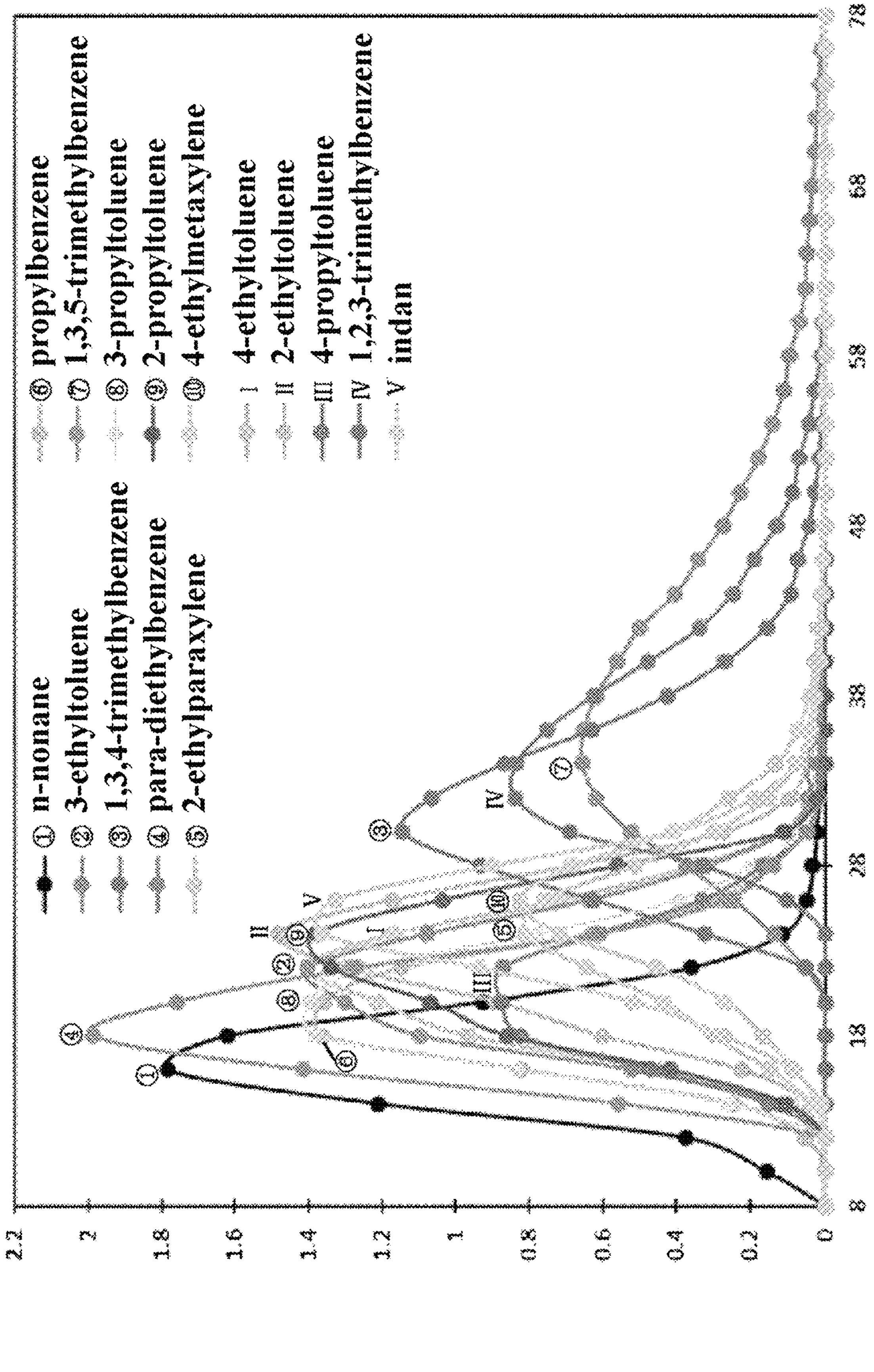
FIG. 1 shows a pulse diagram of the adsorption separation of heavy aromatic hydrocarbon using a pulse device and a highly selective adsorbent of the present invention, wherein n-nonane is used as a tracer, and the heavy aromatic hydrocarbon components are 4-ethyltoluene, 3-ethyltoluene, 2-ethyltoluene, propylbenzene, 4-propyltoluene, 3-propyltoluene, 2-propyltoluene, para-diethylbenzene, 1,3,5-trimethylbenzene, 1,2,4-trimethylbenzene, 1,2,3-trimethylbenzene, 2-ethylparaxylene, 4-ethylmetaxylene, and indan.

The specific embodiments of the present invention are described in detail below, but it should be pointed out that the scope of protection of the present invention is not limited by these specific embodiments, but is determined by the claims in the appendix.

All publications, patent applications, patents, and other references mentioned in this specification are hereby incorporated by reference. Unless otherwise defined, all technical and scientific terms used in this specification have the meaning commonly understood by those skilled in the art. In case of conflict, the definitions in this specification shall control.

When materials, substances, methods, steps, devices, components, or the like are described herein as being “well-known to those skilled in the art”, “prior art”, or the like, they are intended to cover those commonly used in the art at the time of filing, and those that are not commonly used at the present time but will become known in the art as being useful for a similar purpose.

In the context of this specification, except for what is explicitly stated, any item or matter not mentioned is directly applicable to those known in the art without any changes. Moreover, any embodiment described herein can be freely combined with one or more other embodiments described herein, and the technical solutions or technical ideas thus formed shall be regarded as a part of the original disclosure or content of this invention and shall not be considered to be a new matter that has not been disclosed or expected herein, unless those skilled in the art believe that the combination is obviously unreasonable.

In the context of this specification, “exemplary” means “used as illustration, example, or explanatory”. Any example explained here as “exemplary” need not be interpreted as superior or better than other examples. Although various aspects of examples are shown in the drawings, it is not necessary to depict the drawings to scale unless otherwise specified.

In the present invention, trimethylbenzene-based compounds refer to a mixture of 1,2,4-trimethylbenzene, 1,3,5-trimethylbenzene and 1,2,3-trimethylbenzene in any proportion. In addition, trimethylbenzene-based compounds can also represent any one of 1,2,4-trimethylbenzene, 1,3,5-trimethylbenzene and 1,2,3-trimethylbenzene, or a mixture of any two of 1,2,4-trimethylbenzene, 1,3,5-trimethylbenzene and 1,2,3-trimethylbenzene in any proportion.

A first aspect of the present invention provides an adsorbent for trimethylbenzene-based compounds (hereinafter, sometimes also referred to as an adsorbent or a highly selective adsorbent), which is characterized in that, relative to the total amount of X-type molecular sieve and matrix, it comprises 93-99 wt % of X-type molecular sieve and 1-7 wt % of matrix, the matrix is a substance after crystal transformation through in-situ crystallization of clay mineral, the adsorbent is modified with at least one bivalent cation selected from $Mg^{2+}$, $Ca^{2+}$, $Sr^{2+}$, $Fe^{2+}$, $Co^{2+}$, $Ni^{2+}$ and $Zn^{2+}$ (preferably $Sr^{2+}$) and optionally modified with at least one monovalent cation selected from $Li^+$, $Na^+$, $K^+$, $Rb^+$ and $Cs^+$ (preferably $Li^+$).

In an embodiment of the present invention, the bivalent cation is preferably Sr2+. As a result, the preferential selectivity of the adsorbent for trimethylbenzene-based compounds can be significantly increased.

In an embodiment of the present invention, the monovalent cation is preferably Li+. As a result, the adsorption capacity of the adsorbent for trimethylbenzene-based compounds can be increased.

In an embodiment of the present invention, the adsorbent has a water mass fraction of 1-10%, preferably 2-8%, more preferably 2.5-6.0%.

In an embodiment of the present invention, the adsorbent has a BET specific surface area of not less than 560 $m^2/g$, preferably not less than 590 $m^2/g$.

In an embodiment of the present invention, the exchange degree of the bivalent cations of the adsorbent is not particularly limited. When performing the subsequent ion exchange step, sufficient ion exchange is usually performed until an ion exchange equilibrium is reached. In order to achieve the adsorption effect of trimethylbenzene-based compounds of the present invention, the exchange degree of bivalent cations is usually not less than 75%, preferably not less than 85%, more preferably not less than 93%.

In an embodiment of the present invention, the adsorbent has a crushing rate at 130 N of 0.3%-1.0%, preferably 0.3%-0.6%. In the present invention, the method for measuring the crushing rate at 130 N is described below.

In an embodiment of the present invention, the adsorbent has a bulk density of 0.40-0.95 $g/cm^3$, preferably 0.75-0.78 $g/cm^3$. In the present invention, the bulk density is an ignition-based bulk density, and the measurement method is described below. In an embodiment of the present invention, the X-type molecular sieve in the adsorbent has a crystal particle size of 0.5-2.0 micron.

Without wishing to be bound by theory, it is believed that the crystal particle size of the molecular sieve will affect the mass transfer and strength of the adsorbent. The larger the crystal particle size, the worse the mass transfer capacity of the heavy aromatic hydrocarbon raw material and the desorbent in the adsorbent, which in turn affects the efficiency of adsorption separation. If the crystal particle size is too small, the strength of the adsorbent will be reduced, thus affecting the life of the adsorbent.

In an embodiment of the present invention, the X-type molecular sieve in the adsorbent has a molar ratio of silica to alumina of 2.0-2.6, preferably 2.0-2.4.

Without wishing to be limited by theory, it is believed that the molar ratio of silica to alumina in the molecular sieve will also have a significant impact on the adsorption capacity of the adsorbent. If the molar ratio is too high, the selectivity of the adsorbent will become poor, while the too low molar ratio will not only reduce the adsorption capacity of the adsorbent, but also change the internal structure of the molecular sieve.

Through long-term research and practice, the inventors of the present invention have found the range of the crystal particle size of the molecular sieve and the range of the molar ratio of silica to alumina, which is suitable for separating trimethylbenzene monomers.

In an embodiment of the present invention, the clay mineral is selected from non-metal clay minerals.

In an embodiment of the present invention, the clay mineral is at least one of kaolin mineral, bentonite mineral, attapulgite mineral, sepiolite mineral, and illite mineral. In an embodiment of the present invention, the kaolin mineral is at least one of kaolinite, dickite, nacrite, firestone, and halloysite. The mass fraction of crystallized substance in the kaolin mineral is at least 92%, preferably 94%-99%.

In an embodiment of the present invention, the bentonite mineral is at least one of activated clay, natural bleaching earth, and organobentonite.

A second aspect of the present invention provides a method for preparing an adsorbent for trimethylbenzene-based compounds, characterized in that said method comprises the following steps:

(1) shaping into particles: mixing an X molecular sieve and a clay mineral at a mass ratio of 91-98:2-9, shaping into particles, optionally drying, and then calcining at 500 °C-680 °C;

(2) in-situ crystallization: treating calcined particles with an alkali solution and then drying to produce particles as matrix, the concentration of hydroxide ions in the alkali solution is 0.2 mol/L-2.0 mol/L (preferably 0.2 mol/L-1.6 mol/L), (3) ion exchange: subjecting the particles as matrix obtained in step (2) to the cation exchange with an exchange solution of a compound containing at least one bivalent cation selected from $Mg^{2+}$, $Ca^{2+}$, $Sr^{2+}$, $Fe^{2+}$, $Co^{2+}$, $Ni^{2+}$ and $Zn^{2+}$ (preferably $Sr^{2+}$), and optionally a compound containing at least one monovalent cation selected from $Li^+$, $Na^+$, $K^+$, $Rb^+$ and $Cs^+$ (preferably $Li^+$), and then drying the ion-exchanged solid.

In an embodiment of the present invention, in the step of shaping into particles, the manner of mixing X molecular sieve and clay mineral is not particularly limited. It can be a conventional method for manufacturing particles in the art, such as ball-rolling and shaping, kneading-shaping, and extrusion-shaping. In an embodiment of the present invention, the step of shaping into particles is to mix X molecular sieve and clay mineral, and then ball-rolling and shaping. In this case, an equipment such as a powerful mixing and ball-rolling machine can be used. In the case of ball-rolling and shaping, the uniformly mixed solid raw materials are put into the rotating equipment. The stirring paddle and the roller run in reverse, and water is sprayed while rolling. The high-speed rotating stirring paddle contacts the material, instantly generating local high pressure, causing a part of the material to adhere together. At the same time, under the action of the roller, the solid powder adheres and agglomerates into small balls, making the small balls more dense.

In an embodiment of the present invention, upon shaping into particles (for example ball-rolling and shaping) the addition amount of water is 5%-30%, preferably 10%-20% of the total mass of the solid.

In an embodiment of the present invention, the drying condition during shaping into particles is not particularly limited, the drying can be performed at 50 °C-100 °C for 2 hours to 10 hours. In order to convert clay minerals into crystal-like substances, it is necessary to perform the calcining. The calcining temperature is 500 °C-680 °C, preferably 530 °C-650 °C.

In an embodiment of the present invention, the calcining time during shaping into particles is not particularly limited, and it can be 2.0 hours-5.0 hours. After calcining, the kaolin in small balls is converted into a crystal-like substance, which is conducive to its crystal transformation into an FAU-type molecular sieve during the in-situ crystallization step.

In an embodiment of the present invention, the step of shaping into particles comprises mixing an X molecular sieve and a clay mineral at a mass ratio of 91-98:2-9 evenly, ball-rolling and shaping, drying and then calcining at 500 °C-680 °C. In an embodiment of the present invention, the clay mineral is selected from non-metal clay minerals.

In an embodiment of the present invention, the clay mineral is at least one of kaolin mineral, bentonite mineral, attapulgite mineral, sepiolite mineral, and illite mineral. In an embodiment of the present invention, the kaolin mineral is selected from kaolinite, dickite, nacrite, firestone, halloysite or mixtures thereof. The mass fraction of crystallized substance in the kaolin mineral is at least 92%, preferably 94%-99%.

In an embodiment of the present invention, the bentonite mineral is at least one of activated clay, natural bleaching earth, and organobentonite.

In the present invention, clay mineral plays the role of binders, so that the starting X-type molecular sieve powder adheres and agglomerates into particles (such as small balls) during the step of shaping into particles (e.g., ball-rolling and shaping) and has enhanced mechanical strength.

In an embodiment of the present invention, in the step of shaping into particles (for example ball-rolling and shaping), particles (for example small balls) are formed, and screened. Particles (for example small balls) having a certain particle diameter range (for example it can be 400 micron to 950 micron, preferably 450 micron to 900 micron, more preferably 500 micron to 800 micron) are dried and calcined.

In an embodiment of the present invention, in the step of in-situ crystallization, the alkali solution is a solution of at least one of lithium hydroxide, potassium hydroxide, sodium hydroxide, and ammonium hydroxide, preferably a mixed solution of sodium hydroxide and potassium hydroxide.

In an embodiment of the present invention, in the step of in-situ crystallization, in the case that the alkali solution contains Na ions and K ions, the molar ratio of K/(Na+K) in the alkali solution is 0-0.50, preferably 0.15-0.40.

Without being limited by theory, it is believed that using a mixed solution of sodium hydroxide and potassium hydroxide helps to increase the bulk density of the adsorbent of the present invention and reduce its crushing rate. High bulk density and low crushing rate are extremely beneficial to the adsorption separation process of trimethylbenzenes, which can increase the loading degree of the adsorbent, thereby increasing the production capacity of the adsorption separation process, and increasing the service life of the adsorbent.

In an embodiment of the present invention, in the step of in-situ crystallization, the liquid/solid ratio of the alkali solution to the calcined particles is 1.5 L/kg-5.0 L/kg, preferably 2.0 L/kg-4.5 L/kg, more preferably 2.5 L/kg-4.0 L/kg.

In an embodiment of the present invention, in the step of in-situ crystallization, the crystallization temperature is 80

°C-100 °C, preferably 85 °C-99 °C, more preferably 90-98 °C. The crystallization time is not particularly limited, and it can be 1-8 hours.

In an embodiment of the present invention, in the step of in-situ crystallization, the particles as matrix treated with an alkali solution are optionally washed with water. At this time, water washing can be performed until the pH is 7-10.

In an embodiment of the present invention, in the step of in-situ crystallization, the particles as matrix obtained after drying have a particle size of 400 micron to 950 micron, preferably 450 micron to 900 micron, more preferably 500 micron to 800 micron.

In an embodiment of the present invention, in the step of in-situ crystallization, the drying temperature and condition are not particularly limited, the drying can be performed at 50 °C-100 °C for 2 hours to 10 hours.

It is believed that by rationally selecting the conditions for in-situ crystallization, such as the alkali solution composition and concentration, the liquid/solid ratio, and the crystallization temperature, the efficiency of the in-situ crystallization can be improved, the crystallization effect can be improved, and the adsorption capacity of the finally formed adsorbent for trimethylbenzenes can be improved.

In the ion exchange, the particles as matrix after the in-situ crystallization are subjected to the cation exchange. The particles as matrix after the in-situ crystallization are contacted with a cationic solution to exchange the cations to the cationic sites in the molecular sieve.

In an embodiment of the present invention, in the step of ion exchange, it comprises using an exchange solution of the compound containing at least one bivalent cation selected from Mg2+, Ca2+, Sr2+, Fe2+, Co2+, Ni2+ and Zn2+, subjecting the particles as matrix obtained in step (2) to the cation exchange, and then drying the ion-exchanged solid. It is preferred to use Sr2+ to perform the ion exchange, which can significantly increase the preferential selectivity of the adsorbent for trimethylbenzene-based compounds.

In an embodiment of the present invention, in the step of ion exchange, it comprises optionally using an exchange solution of the compound containing at least one monovalent cation selected from Li+, Na+, K+, Rb+ and Cs+ (preferably Li+), subjecting the particles as matrix obtained in step (2) to the cation exchange, and then drying the ion-exchanged solid.

In an embodiment of the present invention, in the step of ion exchange, the exchange solution of the compound containing at least one bivalent cation selected from Mg2+, Ca2+, Sr2+, Fe2+, Co2+, Ni2+ and Zn2+ and the exchange solution of the compound containing at least one monovalent cation selected from Li+, Na+, K+, Rb+ and Cs+ (preferably Li+) can be two exchange solutions that are independently used. In this case, the concentration of the bivalent cation and the concentration of the monovalent cation respectively refer to their respective concentrations of two exchange solutions. During the ion exchange, two exchange solutions are used respectively to perform the ion exchange, and their order is not limited.

In an embodiment of the present invention, in the step of ion exchange, the exchange solution of the compound containing at least one bivalent cation selected from Mg2+, Ca2+, Sr2+, Fe2+, Co2+, Ni2+ and Zn2+ and the exchange solution of the compound containing at least one monovalent cation selected from Li+, Na+, K+, Rb+ and Cs+ (preferably Li+)

can also be a combined exchange solution. In this case, the concentration of the bivalent cation and the concentration of the monovalent cation are the concentration of the bivalent cation and the concentration of the monovalent cation in the combined solution. During the ion exchange, the combined exchange solution may be used.

In an embodiment of the present invention, in the step of ion exchange, the compound containing at least one bivalent cation selected from $Mg^{2+}$, $Ca^{2+}$, $Sr^{2+}$, $Fe^{2+}$, $Co^{2+}$, $Ni^{2+}$ and $Zn^{2+}$ (preferably $Sr^{2+}$) is at least one of nitrate and chloride of each compound.

In an embodiment of the present invention, in the step of ion exchange, the compound containing at least one monovalent cation selected from Li+, Na+, K+, Rb+ and Cs+ (preferably Li+) is at least one of nitrate, chloride and carbonate of each compound.

In an embodiment of the present invention, in the step of ion exchange, in the exchange solution, the concentration of the bivalent cation can be a conventional concentration in the art, for example it can be 0.1 mol/L-1.0 mol/L, preferably 0.15 mol/L-0.8 mol/L, more preferably 0.2 mol/L-0.6 mol/L.

In an embodiment of the present invention, in the step of ion exchange, in the exchange solution, the concentration of the monovalent cation can be a conventional concentration in the art, for example it can be 0.05 mol/L to 0.6 mol/L, preferably 0.08 mol/L to 0.5 mol/L, more preferably 0.1 mol/L to 0.4 mol/L.

In an embodiment of the present invention, in the step of ion exchange, in the exchange solution, the concentration of the bivalent cation is not less than 0.15 mol/L.

In an embodiment of the present invention, in the step of ion exchange, the volume ratio of the exchange solution to the particles is not less than 3.

In an embodiment of the present invention, in the step of ion exchange, the molar ratio of the bivalent cation to the monovalent cation in the exchange solution is not less than 3, preferably not less than 4. At this time, in the case that the exchange solution containing bivalent cations and the exchange solution containing monovalent cations are each independent exchange solutions, the above molar ratio can be achieved by controlling the molar concentration of bivalent cations of the exchange solution containing bivalent cations and the molar concentration of monovalent cations of the exchange solution containing monovalent cations. In the case that the exchange solution containing bivalent cations and the exchange solution containing monovalent cations are a combined exchange solution, the above molar ratio is achieved by controlling the molar concentration of bivalent cations and the molar concentration of monovalent cations in the exchange solution. In an embodiment of the present invention, the manner of the cation exchange can be a conventional manner in the art, for example, the particles as matrix are impregnated in a solution containing the desired cation to be exchanged, or the cation exchange can be carried out in a kettle or column container, preferably continuously in a column container. The conditions for ion exchange are not particularly limited as long as sufficient ion exchange is performed. For example, the exchange temperature is 80 °C-120 °C, preferably is 90 °C-100 °C, the time is 6 hours to 25 hours, preferably 8 hours to 15 hours, the volumetric space velocity of the exchange solution is 2 h-1 to 8 h-1, preferably 3 h-1 to 5 h-1.

In an embodiment of the present invention, in the step of in-situ crystallization, the cation exchanged particles as matrix are optionally washed with water. At this time, water washing can be performed until the pH is 7-10.

Then, the cation-exchanged particles as matrix are dried. Drying can be carried out under normal conditions. For example, it is carried out in flowing hot air or nitrogen, the drying temperature is 50 °C-100 °C, preferably 60 °C-90 °C, and the drying time is 10 hours to 20 hours.

In an embodiment of the present invention, sufficient ion exchange is performed until ion exchange equilibrium is reached. Usually, the exchange degree of the bivalent cation for the metal ion of the adsorbent is not less than 75%, preferably not less than 85%, more preferably not less than 93%.

In an embodiment of the present invention, the water mass fraction of the adsorbent is 1-10%, preferably 2-8%, more preferably 2.5-6.0%.

In an exemplary embodiment of the present invention, the adsorbent of the present invention is prepared by the following method:

(1) ball-rolling and shaping: mixing an X molecular sieve and a clay mineral at a mass ratio of 91-98:2-9 evenly, ball-rolling and shaping, drying and then calcining at 500 °C-680 °C;

(2) in-situ crystallization: small balls obtained after calcining are treated with a mixed solution of sodium hydroxide and potassium hydroxide, so that the clay mineral therein is in-situ crystallized to an FAU-type molecular sieve, which is dried to produce small balls as matrix, the K/(Na+K) molar ratio in the mixed solution of sodium hydroxide and potassium hydroxide is 0-0.50, the concentration of hydroxide ions is 0.2 mol/L-2.0 mol/L;

(3) ion exchange: subjecting small balls as matrix obtained in the in-situ crystallization to the cation exchange with the exchange solution of the compound containing at least one bivalent cation selected from Mg2+, Ca2+, Sr2+, Fe2+, Co2+, Ni2+ and Zn2+ (preferably Sr2+), and optionally the exchange solution of the compound containing at least one monovalent cation selected from Li+, Na+, K+, Rb+ and Cs+ (preferably Li+), and then drying the ion-exchanged solid.

In the preparation method of the adsorbent of the present invention, X-type molecular sieve is mixed with clay mineral as binder, and the obtained particles (small balls) are calcined at high temperature (500 °C-680 °C) to make the clay therein convert into a crystal-like substance, then an alkali-treatment is performed to cause in-situ crystallization and conversion into a FAU-type molecular sieve, and then ion exchange is performed to produce the adsorbent of the present invention. The prepared adsorbent has excellent preferential selectivity for adsorbing trimethylbenzene-based compounds, compression strength and bulk density.

In an embodiment of the present invention, after step (3), the method further comprises (4) activation step: activating the dried product of step (3), preferably at an activation temperature of 150 °C-260 °C, more preferably 180 °C-250 °C. In an embodiment of the present invention, the activation time is 3-10 hours. In an embodiment of the present invention, activation is performed in a nitrogen atmosphere.

In an embodiment of the present invention, the adsorbent provided by the present invention has relatively high compression strength, bulk density and preferential selectivity for adsorbing trimethylbenzene-based compounds.

A method of measuring the crushing rate of a certain volume of sample under an accumulation pressure with the DL-II type particle strength meter (Dalian Chemical Industry Research Design Institute) is used to characterize its compression strength. The measured adsorbent has a crushing rate at 130N of 0.3%-1.0%, preferably 0.3%-0.6%. A method of using a vibrating densitometer, thoroughly vibrating a certain mass of adsorbent particles under specified conditions to determine the vibrating volume, then dividing the sample mass by the vibrating volume to obtain the nature-based bulk density; and then multiplying the nature-based bulk density by the ignition-based percentage content of the sample to obtain its ignition-based bulk density is used, and the measured ignition-based bulk density is 0.40-0.95 g/cm$^3$, preferably 0.75-0.78 g/cm$^3$, which is very beneficial for the adsorption separation of trimethylbenzene mixture from heavy aromatic hydrocarbon.

A third aspect of the present invention provides a separation method for trimethylbenzene-based compounds (hereinafter, sometimes also referred to as the separation method of the present invention), comprising the following steps, adsorption separation: contacting a heavy aromatic hydrocarbon raw material containing trimethylbenzene-based compounds with the adsorbent of the present invention or the adsorbent prepared with the preparation method according to the present invention to adsorb trimethylbenzene-based compounds, and then performing the separation to produce trimethylbenzene-based compounds.

In an embodiment of the present invention, the heavy aromatic hydrocarbon raw material is especially a C9+ heavy aromatic hydrocarbon (that is, a heavy aromatic hydrocarbon rich in C9 and higher aromatic hydrocarbons), and is selected from reforming product, pyrolysis gasoline, naphtha, ethylbenzene-apparatus by-product or catalytically cracked gasoline, preferably a reformed heavy aromatic hydrocarbon fraction, more preferably a reformed heavy aromatic hydrocarbon fraction having a boiling point of 150 °C or higher.

In an embodiment of the present invention, the heavy aromatic hydrocarbon raw material is a reformed heavy aromatic hydrocarbon having a total mass fraction of trimethylbenzene-based compounds of 20% or higher.

In an embodiment of the present invention, relative to the unit mass of adsorbent, the flow rate of the heavy aromatic hydrocarbon raw material is not less than 0.16 kg/(h·kg adsorbent), preferably not less than 0.20 kg/(h·kg adsorbent), more preferably not less than 0.23 kg/(h·kg adsorbent).

In an embodiment of the present invention, trimethylbenzene-based compounds are separated from the adsorbent by using an alkylbenzene (preferably toluene) as desorbent.

In an embodiment of the present invention, it is preferable that trimethylbenzene-based compounds are separated from the adsorbent by using toluene as desorbent.

In an embodiment of the present invention, in the step of adsorption separation, a simulated moving bed apparatus is used, preferably, the simulated moving bed apparatus comprises multiple adsorption beds with loaded adsorbent, each bed has its material injection and withdrawing pipelines, materials that are withdrawn from and injected into the simulated moving bed apparatus divide adsorption beds therein into desorption zone, purification zone, adsorption zone and isolation zone, the adsorption beds between desorbent injection and extract withdrawing constitute the desorption zone, the adsorption beds between extract withdrawing and raw material injection constitute the purification zone, the adsorption beds between raw material injection and raffinate withdrawing constitute the adsorption zone, the adsorption beds between raffinate withdrawing and desorbent injection constitute the isolation zone.

In an embodiment of the present invention, during one step time, the withdrawing and injection order of each material in the material flowing direction of the simulated moving bed is desorbent, extract, raw material and raffinate.

In an embodiment of the present invention, the pressure of the simulated moving bed apparatus constitute is 0.5 MPa-1.2 MPa (preferably 0.6 MPa-1.0 MPa), the temperature is 120 °C-200 °C. (140 °C-180 °C).

In an embodiment of the present invention, the ratio of mass flow rates of the desorbent and the heavy aromatic hydrocarbon raw material injected into the simulated moving bed apparatus (desorbent/heavy aromatic hydrocarbon raw material) is not greater than 3.6, preferably not greater than 3.4, more preferably not greater than 3.2.

In an embodiment of the present invention, the simulated moving bed apparatus comprises an adsorption zone, a purification zone, a desorption zone and an isolation zone, and has a ratio of bed numbers of 29±10%:37±15%:21±5%:13±4%. In an embodiment of the present invention, the simulated moving bed apparatus has one cycle period of 18-60 minutes, preferably 25-35 minutes.

In an embodiment of the present invention, each adsorption bed of the simulated moving bed is provided with a grid, which is equipped with material injection and withdrawing pipelines of said bed, two flushing liquor pipelines are set up in parallel with material injection and withdrawing pipelines of each adsorption bed; each pipeline is provided with an on-off valve, the extract is used as the flushing liquor, the flushing liquor from one flushing liquor pipeline is injected into a bed that is located one bed upstream the raw material injection bed, and the flushing liquor from the other flushing liquor pipeline is injected into a bed that is located 2-4 beds downstream the extract withdrawing position.

In an embodiment of the present invention, the grid of each adsorption bed is equipped with one withdrawing and injection pipeline, and multiple parallel on-off valves are set up on the pipeline to control materials to be withdrawn from and injected into the adsorbent beds.

In an embodiment of the present invention, the withdrawing and injection pipelines of each adsorbent bed are provided with 6-7 on-off valves.

In an embodiment of the present invention, each adsorption bed is provided with a pipeline for which the flushing liquor is used as the desorbent, the injection position of which is one bed upstream the extract withdrawing position.

Figure 2:
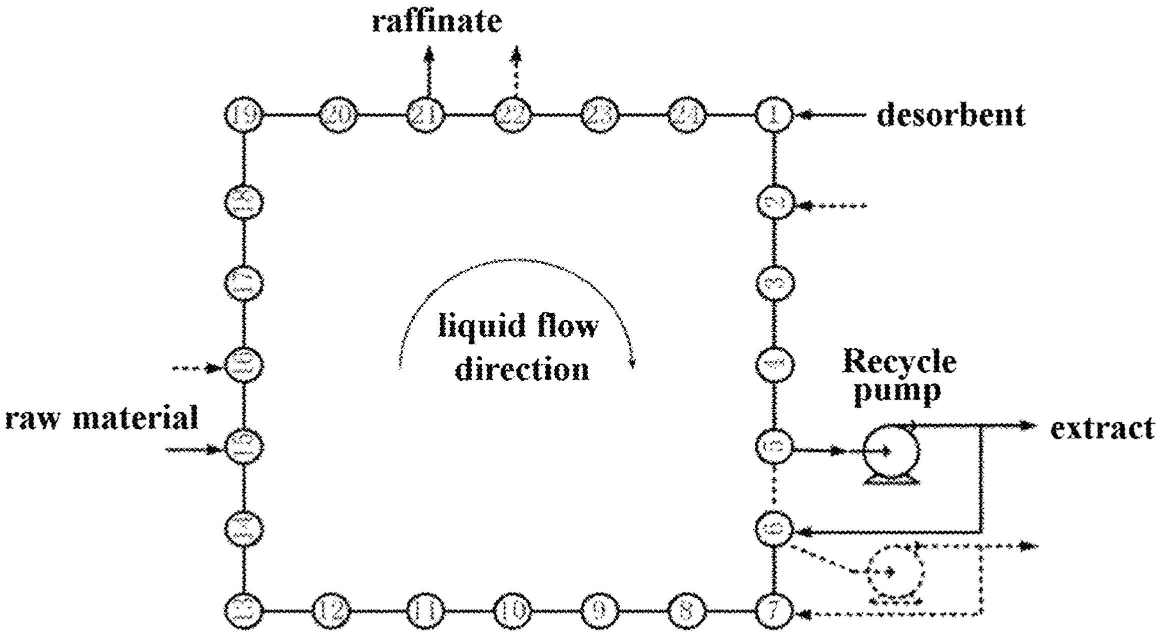
FIG. 2 is a schematic diagram of the small-scale simulated moving bed adsorption separation process of the present invention.

In an embodiment of the present invention, the adsorbent of the present invention is particularly suitable for separating a mixture of trimethylbenzenes from the heavy aromatic hydrocarbon. A heavy aromatic hydrocarbon, preferably a reformed heavy aromatic hydrocarbon is used as raw material and sent to an adsorption separation apparatus, which is a simulated moving bed, wherein the adsorbent is the adsorbent according to the present invention, and the desorbent is an alkylbenzene, preferably toluene. As shown in FIG. 2, the simulated moving bed apparatus of the present invention includes multiple adsorption beds with loaded adsorbent, for example 24 adsorption bed as shown in FIG. 2. Each bed has its material injection and withdrawing pipelines, materials that are withdrawn from and injected into the simulated moving bed divide adsorption beds therein into desorption zone, purification zone, adsorption zone and isolation zone. The adsorption beds between desorbent injection and extract withdrawing constitute the desorption zone, the adsorption beds between extract withdrawing and raw material injection constitute the purification zone, the adsorption beds between raw material injection and raffinate withdrawing constitute the adsorption zone, the adsorption beds between raffinate withdrawing and desorbent injection constitute the isolation zone. The ratio of bed numbers of adsorption zone, purification zone, desorption zone and isolation zone is 29±10%:37±15%:21±5%:13±4%. During the operation of the simulated moving bed, the position of each material withdrawn from and injected into the adsorption beds of the adsorption column can be periodically changed. Multiple-way rotary valves or programmed switch valve groups can be used to control each of the materials to be withdrawn from and injected into different adsorption beds. At a certain moment, each of the materials is connected to a specific bed layer. At a certain interval of time, i.e. one step time, the position for each of the materials withdrawing from and injected into the adsorption bed moves downward by one adsorption bed, as shown in FIG. 2, moving from the solid arrow to the dashed arrow position. The time required for a certain material to be injected into the adsorption bed (or a certain material to be withdrawn from the adsorption bed) to return to the starting position through all adsorption beds is one cycle, which is usually 18 minutes to 60 minutes, preferably 25 minutes to 35 minutes.

The extract obtained by the adsorption separation method of the present invention basically only contains three isomers of trimethylbenzene, and the content of other components is extremely low.

In an embodiment of the present invention, the trimethylbenzene-based compounds obtained from the adsorption separation step have a total purity of not less than 99 wt %.

In an embodiment of the present invention, the separation method of the present invention further comprises a distillation step: trimethylbenzene-based compounds obtained from the adsorption separation are subjected to distillation, to produce 1,3,5-trimethylbenzene, 1,2,4-trimethylbenzene, and 1,2,3-trimethylbenzene respectively.

In an embodiment of the present invention, in the distillation step, an extract stream from the adsorption separation step is sent to a dividing wall column, 1,3,5-trimethylbenzene is produced from the top of the dividing wall column, 1,2,4-trimethylbenzene is produced from the side-line of the dividing wall column, 1,2,3-trimethylbenzene is produced from the bottom of the dividing wall column.

In an embodiment of the present invention, in the distillation step, an extract stream from the adsorption separation step is sent to the first distillation column, 1,3,5-trimethylbenzene is produced by separation from the column top of the first distillation column, the bottom product of the first distillation column is sent to a second distillation column, 1,2,4-trimethylbenzene is produced by separation from the column top of the second distillation column, 1,2,3-trimethylbenzene is produced from the column bottom of the second distillation column.

In an embodiment of the present invention, in the distillation step, an extract stream from the adsorption separation step is sent to the first distillation column, 1,3,5-trimethylbenzene is produced by separation from the column top of the first distillation column, the bottom product of the first distillation column is sent to a second distillation column, 1,2,4-trimethylbenzene is produced by separation from the column top of the second distillation column, the bottom product of the second distillation column is sent to a third distillation column, 1,2,3-trimethylbenzene is produced by separation from the column top of the third distillation column, the bottom product is an aromatic solvent oil with high boiling point.

In an embodiment of the present invention, in the distillation step, an extract stream from the adsorption separation step is sent to the first distillation column, 1,3,5-trimethylbenzene is produced by separation from the column top of the first distillation column, the column bottom stream is a mixture of 1,2,4-trimethylbenzene and 1,2,3-trimethylbenzene, 1,2,4-trimethylbenzene and 1,2,3-trimethylbenzene are further separated by using a crystallization process.

In an embodiment of the present invention, in the distillation step, 1,2,3-trimethylbenzene can be separated from an extract stream from the adsorption separation step by using a crystallization process, a mixture stream of the residual 1,2,4-trimethylbenzene and 1,3,5-trimethylbenzene is sent to the first distillation column, 1,3,5-trimethylbenzene is produced by separation from the column top of the first distillation column, the column bottom stream is 1,2,4-trimethylbenzene.

In an embodiment of the present invention, 1,3,5-trimethylbenzene, 1,2,4-trimethylbenzene, and 1,2,3-trimethylbenzene obtained from the distillation step have purities of not less than 97.0 wt %, 98.0 wt % and 95.0 wt %, preferably not less than 98.5 wt %, 99.3 wt % and 97.0 wt % respectively.

Figure 3:
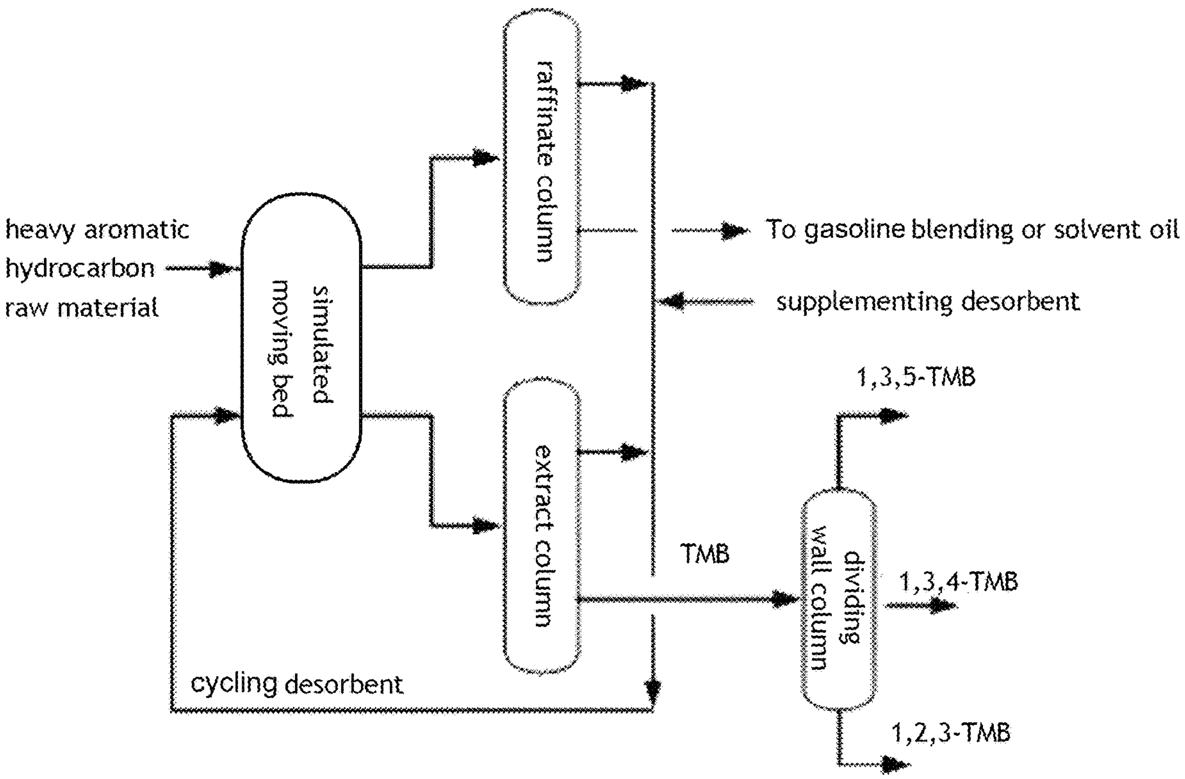
FIG. 3 is a schematic diagram of an apparatus for the combined process of adsorption separation and distillation of the present invention.

In an embodiment of the present invention, as shown in FIG. 3, the heavy aromatic hydrocarbon raw material flows through the adsorption separation to produce an extract stream and a raffinate stream, which are respectively sent to the extract column and the raffinate column. After recovering the desorbent for recycling use, trimethylbenzene-based compounds (a mixture of three trimethylbenzenes) with a purity of not less than 99 wt % are produced from the column bottom of the extract column, and the extract is sent to the distillation process for further separation. The other heavy aromatic hydrocarbon components other than trimethylbenzene obtained from the column bottom of the raffinate column are continuously utilized as the gasoline blending component, or the aromatic solvent oil component with high boiling point. As shown in FIG. 3, a dividing wall column can be used in the distillation process. the bottom of the extract column of the adsorption separation process is sent to a dividing wall column, 1,3,5-trimethylbenzene can be produced from the top of the dividing wall column, 1,2,4-trimethylbenzene is produced from the side-line, and 1,2,3-trimethylbenzene is produced from the column bottom. In another embodiment of the present invention, two distillation columns connected in series can also be used in the distillation process. The bottom of the extract column of the adsorption separation process is sent to the first distillation column, the top product is 1,3,5-trimethylbenzene, and the bottom product is a mixture stream of 1,2,4-trimethylbenzene and 1,2,3-trimethylbenzene. The mixture stream is subsequently sent to a second distillation column, the top product is 1,2,4-trimethylbenzene, the bottom product is 1,2,3-trimethylbenzene. A mixture of three trimethylbenzenes obtained from the adsorption separation can also be separated with a combined process of distillation and crystallization. The mixture stream is sent to the first distillation column, 1,3,5-trimethylbenzene can be produced from the column top, and the column bottom is a mixture of 1,2,4-trimethylbenzene and 1,2,3-trimethylbenzene, which can be separated with a crystallization process.

In an embodiment of the present invention, the separation method of the present invention further comprises an isomerization step, the isomerization step is between the adsorption separation and the distillation step, and trimethylbenzene-based compounds are subjected to the isomerization, or the isomerization step is after the distillation step, at least one of 1,3,5-trimethylbenzene, 1,2,4-trimethylbenzene, and 1,2,3-trimethylbenzene is subjected to the isomerization.

In an embodiment of the present invention, after one trimethylbenzene or a mixture of trimethylbenzenes is isomerized, the obtained mixture stream of trimethylbenzenes with a thermodynamic equilibrium concentration is returned to the adsorption separation step for separation.

In an embodiment of the present invention, in the distillation step, in the case of using two distillation columns, the stream sent to the isomerization unit is produced from the side-line of first distillation column; or, in the distillation step, in the case of using three distillation columns, the stream sent to the isomerization unit is produced from the side-line of the first distillation column or the second distillation column.

In an embodiment of the present invention, the separation method of the present invention further comprises a raffinate separation step: raffinate from the simulated moving bed apparatus is subjected to distillation to produce a desorbent and a heavy aromatic hydrocarbon component in which trimethylbenzene-based compounds have been separated by adsorption.

In an embodiment of the present invention, as shown in FIG. 3, other heavy aromatic hydrocarbon components other than trimethylbenzene-based compounds obtained from the column bottom of the extraction column can be further utilized as gasoline blending component or aromatic solvent oil component with high boiling point, significantly increasing the economic added value of heavy aromatic hydrocarbon products and bringing considerable economic benefits.

In an embodiment of the present invention, the separation method of the present invention comprises an adsorption separation and a distillation process, wherein the heavy aromatic hydrocarbon raw material is subjected to an adsorption separation process, and the desorbent is recovered from the extract to produce a mixture stream of three isomers, namely 1,3,5-trimethylbenzene, 1,2,4-trimethylbenzene, and 1,2,3-trimethylbenzene. The mixture stream of three isomers is then subjected to the distillation process to produce corresponding monomers. The desorbent is recovered from the raffinate of the adsorption separation process to produce gasoline blending component or aromatic solvent oil component with high boiling point, wherein the adsorbent of the present invention or the adsorbent prepared with the preparation method according to the present invention is used in the adsorption separation process.

A fourth aspect of the present invention provides a separation apparatus for trimethylbenzene-based compounds (hereinafter, sometimes also referred to as a separation apparatus of the present invention), which includes the following units, adsorption separation unit: having the adsorbent according to the present invention or the adsorbent prepared with the preparation method according to the present invention, and used to adsorb and separate trimethylbenzene-based compounds from a heavy aromatic hydrocarbon raw material containing trimethylbenzene-based compounds to produce trimethylbenzene-based compounds.

In an embodiment of the present invention, the adsorption separation unit can be arbitrary, as long as it has the adsorbent of the present invention or the adsorbent prepared with the preparation method according to the present invention. For example, the adsorption separation unit can be a chromatographic column, a moving bed, a displacement chromatography, a multiple-column adsorption, a pressure swing adsorption device and the like filled with the adsorbent of the present invention or the adsorbent prepared with the preparation method according to the present invention.

In an embodiment of the present invention, the adsorption separation unit adopts a simulated moving bed, preferably, the simulated moving bed comprises multiple adsorption beds with loaded adsorbent, each bed has its material injection and withdrawing pipelines, materials that are withdrawn from and injected into the simulated moving bed apparatus divide adsorption beds therein into desorption zone, purification zone, adsorption zone and isolation zone, the adsorption beds between desorbent injection and extract withdrawing constitute the desorption zone, the adsorption beds between extract withdrawing and raw material injection constitute the purification zone, the adsorption beds between raw material injection and raffinate withdrawing constitute the adsorption zone, the adsorption beds between raffinate withdrawing and desorbent injection constitute the isolation zone. In an embodiment of the present invention, in the case that the adsorption separation unit adopts a simulated moving bed, the simulated moving bed apparatus comprises an adsorption zone, a purification zone, a desorption zone and an isolation zone, and has a ratio of bed numbers of 29±10%:37±15%:21±5%:13±4%.

In an embodiment of the present invention, in the case that the adsorption separation unit adopts a simulated moving bed, each adsorption bed of the simulated moving bed is provided with a grid, which is equipped with material injection and withdrawing pipelines of said bed, two flushing liquor pipelines are set up in parallel with material injection and withdrawing pipelines of each adsorption bed; each pipeline is provided with an on-off valve, the extract is used as the flushing liquor, the flushing liquor from one flushing liquor pipeline is injected into a bed that is located one bed upstream the raw material injection bed, and the flushing liquor from the other flushing liquor pipeline is injected into a bed that is located 2-4 beds downstream the extract withdrawing position.

In an embodiment of the present invention, in the case that the adsorption separation unit adopts a simulated moving bed, the grid of each adsorption bed is equipped with one withdrawing and injection pipeline, and multiple parallel on-off valves are set up on the pipeline to control materials to be withdrawn from and injected into the adsorbent beds.

In an embodiment of the present invention, in the case that the adsorption separation unit adopts a simulated moving bed, the withdrawing and injection pipelines of each adsorbent bed are provided with 6-7 on-off valves.

In an embodiment of the present invention, in the case that the adsorption separation unit adopts a simulated moving bed, each adsorption bed is provided with a pipeline for which the flushing liquor is used as the desorbent, the injection position of which is one bed upstream the extract withdrawing position.

In an embodiment of the present invention, the separation apparatus of the present invention further comprises a distillation unit, which is connected to the downstream of the adsorption separation unit, receives a stream containing trimethylbenzene-based compounds from the adsorption separation unit, and performs the distillation to produce 1,3,5-trimethylbenzene, 1,2,4-trimethylbenzene, and 1,2,3-trimethylbenzene respectively.

In an embodiment of the present invention, the distillation unit comprises a dividing wall column, to which the extract stream from the adsorption separation step is introduced, the column top of the dividing wall column is provided with 1,3,5-trimethylbenzene discharge outlet, the side-line of the dividing wall column is provided with 1,2,4-trimethylbenzene discharge outlet, the column bottom of the dividing wall column is provided with 1,2,3-trimethylbenzene discharge outlet.

In an embodiment of the present invention, the distillation unit comprises a first distillation column and a second distillation column successively connected in series, the column bottom of the first distillation column is connected to the second distillation column, the column top of the first distillation column is provided with a discharge outlet for 1,3,5-trimethylbenzene, the column top of the second distillation column is provided with a discharge outlet for 1,2,4-trimethylbenzene, the column bottom of the second distillation column is provided with a discharge outlet for 1,2,3-trimethylbenzene.

In an embodiment of the present invention, the distillation unit comprises a first distillation column, a second distillation column and a third distillation column successively connected in series the column bottom of the first distillation column is connected to the second distillation column, the column top of the first distillation column is provided with a discharge outlet for 1,3,5-trimethylbenzene, the column bottom of the second distillation column is connected to the third distillation column, the column top of the second distillation column is provided with a discharge outlet for 1,2,4-trimethylbenzene, the column top of the third distillation column is provided with a discharge outlet for 1,2,3-trimethylbenzene, the column bottom of the third distillation column is provided with a discharge outlet for aromatic solvent oil with high boiling point.

In an embodiment of the present invention, the separation apparatus of the present invention further comprises a raffinate distillation unit, which is connected to the downstream of the adsorption separation unit, receives a stream containing a heavy aromatic hydrocarbon component in which trimethylbenzene-based compounds have been separated by adsorption from the adsorption separation unit, and in which the distillation is performed to produce a heavy aromatic hydrocarbon component in which trimethylbenzene-based compounds have been separated by adsorption and a desorbent respectively.

In an embodiment of the present invention, the separation apparatus of the present invention further comprises an isomerization unit, which is located between the adsorption separation unit and the distillation unit, and used to receive a stream containing trimethylbenzene-based compounds from the adsorption separation unit, and in which the isomerization is performed; or which is connected to the downstream of the distillation unit, used to receive at least one of 1,3,5-trimethylbenzene, 1,2,4-trimethylbenzene, and 1,2,3-trimethylbenzene from the distillation unit, and in which the isomerization is performed.

In an embodiment of the present invention, in the case that the distillation unit has two distillation columns, the side-line of first distillation column is provided with an isomerization stream outlet; or in the case that the distillation unit has three distillation columns, the side-line of the second distillation column has an isomerization stream outlet.

In an embodiment of the present invention, the isomerization unit comprises an isomerization reactor, a gas-liquid separator and a lighter hydrocarbon-removing distillation column, trimethylbenzene-based compounds or any trimethylbenzene monomer is subjected to the isomerization reaction, the resulting mixture stream is sent to a gas-liquid separator, the top of the separator is provided with a gas outlet, hydrogen gas is produced from the top outlet, the bottom is provided with a liquid phase outlet, the liquid phase stream is produced from the bottom of the separator, and sent to the lighter hydrocarbon-removing column, the top of the lighter hydrocarbon-removing column is provided with a lighter hydrocarbon outlet, the lighter hydrocarbon is produced therefrom, the bottom of the lighter hydrocarbon-removing column is provided with an outlet for the stream after the isomerization reaction, the bottom stream is produced from the outlet and then sent to the adsorption separation unit to continue the separation.

A fifth aspect of the present invention provides use of the adsorbent of the present invention or the adsorbent prepared with the preparation method according to the present invention in adsorbing trimethylbenzene-based compounds from the heavy aromatic hydrocarbon.

EXAMPLE

Below is a further detailed explanation of this application through the attached figures and examples. Through these explanations, the characteristics and advantages of this application will become clearer and more definitive.

The present invention is further explained through examples below, but the present invention is not limited thereto.

The methods for determining toluene adsorption capacity, ignition-based bulk density, strength, BET specific surface area, water mass fraction, and metal exchange degree are described below.

To evaluate the physicochemical properties of the adsorbent, the present invention uses the following experiments for measurement. The toluene gas-phase adsorption experiment is used to determine the adsorption capacity of the adsorbent. The specific operation method is to contact a certain mass of adsorbent with the nitrogen gas carrying toluene (toluene partial pressure of 0.05 MPa) at 35 °C until toluene reaches the adsorption equilibrium. The adsorption capacity of the tested adsorbent is calculated based on the mass difference of the adsorbent before and after the toluene adsorption using the following formula.

$$C = \frac{m_2 - m_1}{m_1} \times 1000$$

wherein, C is the adsorption capacity, in milligrams per gram; M1 is the mass of the tested adsorbent before adsorbing toluene, in grams; M2 is the mass of the tested adsorbent after adsorbing toluene, in grams.

Method for measuring the ignition-based bulk density of the adsorbent: adding 50 mL of the adsorbent into a 100 mL graduated cylinder, vibrating on a vibrating densitometer (produced by Liaoning Meter Institute Co., Ltd.) for 5 minutes, then adding 50 mL of the adsorbent and vibrating for 5 minutes: the ratio of the mass to the volume of the adsorbent in the graduated cylinder is the bulk density of the adsorbent; and taking a certain mass of the adsorbent and igniting it at 600 °C for 2 hours, and placing it in a desiccator to cool down to room temperature: the ratio of the mass of the adsorbent before the ignition to the mass of the adsorbent after the ignition is the ignition basis, and the product of the ignition base and the bulk density of the adsorbent is the ignition-based bulk density.

The compression strength of the adsorbent is expressed by the crushing rate of the small ball adsorbent under a certain pressure. The lower the crushing rate, the higher the compression strength. Method for determining the compression strength of the adsorbent: DL-II type particle strength meter (produced by Dalian Chemical Industry Research Design Institute) is used to measure the particle strength. After the adsorbent small balls pass through a 300 micron sieve, approximately 1.5 mL of the adsorbent is loaded into a stainless steel cylinder. During the measurement, a thimble that is in interference fit with the stainless steel cylinder is installed and pressed once at the pre-set pressure, the adsorbent is poured out, then passed through a 300 micron sieve and weighed. The reduction amount of the adsorbent mass before and after the pressure test is the crushing rate of the adsorbent at the set pressure, i.e. crushing rate at 300N.

The BET method determines the specific surface area using nitrogen as the adsorbate, helium or hydrogen as the carrier gas. The two gases are mixed in a certain proportion to reach a specified relative pressure, and then flow through the solid material. The adsorption capacity of the sample at this relative pressure can be calculated based on the peak areas of the correction peak and the desorption peak. The specific surface area and the pore volume of the adsorbent are determined with a BET specific surface area determinator.

The method for determining the water mass fraction of the adsorbent is as follows: the temperature of the adsorbent is slowly raised to 600 °C and maintained for several hours until the mass no longer changes. The mass after cooling is taken as the ignition-based mass. the ratio of the difference obtained by subtracting the ignition-based mass from the mass of the adsorbent after activation at different temperatures to the adsorbent mass is the water mass fraction of the adsorbent.

To evaluate the mass fraction of metal ions in the adsorbent structure after ion exchange testing, the mass fraction of metal oxides in the adsorbent was determined using an X-ray fluorescence spectrometer. Based on this, the molar fraction of metal ions is calculated, and the ion exchange degree of the adsorbent is further calculated using the following formula.

$$\eta = \frac{\frac{m_3}{M_3}}{\frac{m_1}{M_1} + \frac{m_2}{M_2}} \times 100$$

wherein, $\eta$ is the ion exchange degree, $m_1$ and $m_2$ are the mass fractions of $Na_2O$ and $K_2O$ in the adsorbent before the ion exchange experiment, $m_3$ is the mass fraction of target metal (metal to be exchanged) oxide in the adsorbent after the ion exchange, $M_1$ and $M_2$ are the molar masses of $Na_2O$ and $K_2O$ in the adsorbent before the ion exchange experiment, and $M_3$ is the molar mass of target metal (metal to be exchanged) oxide in the adsorbent after the ion exchange experiment, the unit of $\eta$ is %.

The adsorption capacity A of the adsorbent for aromatic hydrocarbons in the liquid phase is measured as follows: about 3 g of a powder sample of the dehydrated and activated adsorbent is put into a glass bottle with a polytetrafluoroethylene sealing cap, 18 g of the formulated absorption solution is added dropwise, and the bottle cap is tighten up. The adsorption was performed at a constant temperature of 70 °C for 24 hours, and then a trace amount of the solution was taken for chromatographic analysis. Assuming that n-nonane is not adsorbed at all, it can be used as an internal standard to calculate the adsorption capacity for the heavy aromatic hydrocarbon per unit mass of the adsorbent through the concentration changes of the liquid phase components before and after the adsorption. Total adsorption capacity $A=1000\times m_{solution}\times(1-Z_{n\text{-}nonane,initial}/Z_{n\text{-}nonane})/m_{adsorbent}$, the unit of measurement for A is mg/g, $m_{solution}$ and $m_{adsorbent}$ are the masses of adsorption solution and adsorbent respectively, $Z_{n\text{-}nonane,initial}$ and $Z_{n\text{-}nonane}$ are the mass fractions of n-nonane in adsorption solution respectively in the initial adsorption solution and after adsorption equilibrium, the adsorption capacity of component i in the adsorbent $A_i=1000\lambda m_{solution}\times(Z_{i0}-Z_{n\text{-}nonane,initial}Z_i/Z_{n\text{-}nonane})$, $Z_{i0}$ is the mass fraction of component i in the initial adsorption solution, $Z_i$ is the mass fraction of component i in the adsorption equilibrium solution.

Example 1

Preparation of Highly Selective Adsorbent of the Present Invention.

Highly selective adsorbent was prepared through the following steps:

(1) Ball-rolling and shaping: 93 kg (ignition mass) of NaX molecular sieve powder with a crystal particle size of 0.5-1.0 micron and a $SiO_2/Al_2O_3$ molar ratio of 2.3 and 7 kg of kaolin were mixed evenly, and put into a powerful ball-rolling machine to carry out the stirring while an appropriate amount of deionized water was sprayed so that the solid powder was aggregated into small balls. The amount of water sprayed when rolling the balls was 10% by mass of the solid powder. After screening, small balls with a particle size of 500-800 microns were taken, dried at 90 °C for 5 hours, and calcined at 550 °C for 3 hours.

(2) In-situ crystallization: 65 kg of the calcined small balls from the step of ball-rolling and shaping were placed in 210 liters of a mixed solution of sodium hydroxide and potassium hydroxide. The concentration of hydroxide ions in the mixed solution was 0.4 mol/L, and the K/(Na+K) molar ratio was 0.3. The in-situ crystallization treatment was performed at 90 °C for 3 hours, the in-situ crystallized small balls were water-washed until the pH of the washing solution was less than 10, and dried at 90 °C for 3 hours to obtain small balls as matrix.

(3) Ion exchange: 600 mL of in-situ crystallized and dried small balls as matrix were loaded into an ion-exchange column for cation exchange, and the exchange was continuously performed with 0.40 M strontium chloride solution at a volume space velocity of 5.0 $h^{-1}$ at 96 °C under 0.1 MPa for 8 hours, and the total amount of the used strontium chloride solution was 24 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce a highly selective adsorbent A.

Example 2

The preparation steps were identical to those of Example 1, except for (3) Ion exchange: 600 mL of in-situ crystallized and dried small balls as matrix were loaded into an ion-exchange column for cation exchange, and the exchange was continuously performed with 0.35 M magnesium chloride solution at a volume space velocity of 5.0 $h^{-1}$ at 96 °C under 0.1 MPa for 8 hours, and the total amount of the used magnesium chloride solution was 24 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce a highly selective adsorbent B.

Example 3

The preparation steps were identical to those of Example 1, except for (3) Ion exchange: 600 mL of in-situ crystallized and dried small balls as matrix were loaded into an ion-exchange column for cation exchange, and the exchange was continuously performed with 0.40 M calcium chloride solution at a volume space velocity of 5.0 $h^{-1}$ at 97 °C under 0.1 MPa for 8 hours, and the total amount of the used calcium chloride solution was 24 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce a highly selective adsorbent C.

Example 4

The preparation steps were identical to those of Example 1, except for (3) Ion exchange: 600 mL of in-situ crystallized and dried small balls as matrix were loaded into an ion-exchange column for cation exchange, and the exchange was continuously performed with 0.30 M cobalt chloride solution at a volume space velocity of 5.5 $h^{-1}$ at 98 °C under 0.1 MPa for 8 hours, and the total amount of the used cobalt chloride solution was 24 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce a highly selective adsorbent D.

Example 5

The preparation steps were identical to those of Example 1, except for (3) Ion exchange: 600 mL of in-situ crystallized and dried small balls as matrix were loaded into an ion-exchange column for cation exchange, and the exchange was continuously performed with a mixed solution of 0.15 M lithium chloride and 0.30 M strontium chloride at a volume space velocity of 4.5 $h^{-1}$ at 94 °C under 0.1 MPa for 8 hours, and the total amount of the used lithium chloride solution was 6 L, and the total amount of the used strontium chloride solution was 18 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce a highly selective adsorbent E.

Comparative Example 1

The preparation steps were identical to those of Example 1, except for (3) Ion exchange: 600 mL of in-situ crystallized and dried small balls as matrix were loaded into an ion-exchange column for cation exchange, and the exchange was continuously performed with 0.20 M barium chloride solution at a volume space velocity of 5.0 $h^{-1}$ at 94 °C under 0.1 MPa for 8 hours, and the total amount of the used barium chloride solution was 24 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce an adsorbent F.

The water mass fraction, toluene adsorption capacity, liquid phase static adsorption capacity, BET specific surface area and exchange degree of the prepared adsorbents are shown in Table 1.

TABLE 1

| Example No. | Adsorbent No. | Metal ion | Water mass fraction, % | Toluene adsorption capacity, mg/g | Liquid phase static adsorption capacity, mg/g | BET specific surface area, $m^2/g$ | Exchange degree, % |
|---|---|---|---|---|---|---|---|
| Example 1 | A | Sr | 5.48 | 188 | 155 | 590 | 99 |
| Example 2 | B | Mg | 3.71 | 230 | 180 | 695 | 82 |
| Example 3 | C | Ca | 3.91 | 213 | 166 | 640 | 99 |
| Example 4 | D | Co | 3.57 | 203 | 164 | 629 | 92 |
| Example 5 | E | LiSr | 2.82 | 195 | 160 | 600 | 93 |
| Comparative Example 1 | F | Ba | 4.88 | 175 | 150 | 560 | 98 |

Example 6

Adsorbent was prepared through the following steps:

(1) Ball-rolling and shaping: 93 kg (ignition mass) of NaX molecular sieve powder with a crystal particle size of 0.5-1.0 micron and a $SiO_2/Al_2O_3$ molar ratio of 2.3 and 7 kg of kaolin were mixed evenly, and put into a powerful ball-rolling machine to carry out the stirring while an appropriate amount of deionized water was sprayed so that the solid powder was aggregated into small balls. The amount of water sprayed when rolling the balls was 10% by mass of the solid powder. After screening, small balls with a particle size of 500-800 microns were taken, dried at 90 °C for 5 hours, and calcined at 550 °C for 3 hours.

(2) In-situ crystallization: 65 kg of the calcined small balls from the step of ball-rolling and shaping were placed in 210 liters of a sodium hydroxide hydroxide. The concentration of hydroxide ions in the solution was 0.4 mol/L. The in-situ crystallization treatment was performed at 90 °C for 3 hours, the in-situ crystallized small balls were water-washed until the pH of the washing solution was less than 10, and dried at 90 °C for 3 hours to obtain small balls as matrix.

(3) Ion exchange: 600 mL of in-situ crystallized and dried small balls as matrix were loaded into an ion-exchange column for cation exchange, and the exchange was continuously performed with 0.40 M strontium chloride solution at a volume space velocity of 5.0 $h^{-1}$ at 96 °C under 0.1 MPa for 8 hours, and the total amount of the used strontium chloride solution was 24 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce a highly selective adsorbent G. The water mass fraction, toluene adsorption capacity, liquid phase static adsorption capacity, crushing rate, bulk density and exchange degree of the prepared highly selective adsorbent G are shown in Table 2.

TABLE 2

| Example No. | Water mass fraction, % | Toluene adsorption capacity, mg/g | Liquid phase static adsorption capacity, mg/g | Crushing rate (130N), % | Bulk density, $g/cm^3$ | Exchange degree |
|---|---|---|---|---|---|---|
| Example 1 | 5.48 | 188 | 155 | 0.5 | 0.76 | 99 |
| Example 6 | 5.45 | 185 | 152 | 0.6 | 0.74 | 99 |

As can be seen from Table 2, using a mixed solution of sodium hydroxide and potassium hydroxide for in-situ crystallization could increase the bulk density of the adsorbent and reduce its crushing rate.

Comparative Example 2

Adsorbent of Comparative Example was prepared through the following steps:

(1) Ball-rolling and shaping: 85 kg (ignition mass) of NaX molecular sieve powder with a crystal particle size of 0.5-1.0 micron and a $SiO_2/Al_2O_3$ molar ratio of 2.3 and 15 kg of kaolin were mixed evenly, and put into a powerful ball-rolling machine to carry out the stirring while an appropriate amount of deionized water was sprayed so that the solid powder was aggregated into small balls. The amount of water sprayed when rolling the balls was 10% by mass of the solid powder. After screening, small balls with a particle size of 500-800 microns were taken, dried at 90 °C for 5 hours, and calcined at 550 °C for 3 hours.

The other steps were identical to those of Example 1 to prepare adsorbent H.

The water mass fraction, toluene adsorption capacity, liquid phase static adsorption capacity, crushing rate, bulk density and exchange degree of the prepared adsorbent H are shown in Table 3.

TABLE 3

| Example No. | Water mass fraction, % | Toluene adsorption capacity, mg/g | Liquid phase static adsorption capacity, mg/g | Crushing rate (130N), % | Bulk density, g/cm$^3$ | Exchange degree |
|---|---|---|---|---|---|---|
| Example 1 | 5.48 | 188 | 155 | 0.5 | 0.76 | 99 |
| Comparative Example 2 | 5.49 | 165 | 140 | 0.5 | 0.72 | 90 |

As can be seen from Table 3, in Comparative Example 2, the X molecular sieve and the kaolin mineral were mixed and shaped at a mass ratio of 85:15. The adsorption capacity, bulk density and metal exchange degree of the prepared adsorbent were significantly reduced, reducing the raw material processing capacity of the processing apparatus, further affecting the purity and yield of the target product, and increasing the energy consumption of the apparatus.

Comparative Example 3

(1) Ball-rolling and shaping: 95 kg (ignition mass) of NaA molecular sieve powder with a crystal particle size of 0.5-1.0 micron and a $SiO_2/Al_2O_3$ molar ratio of 1.0, 3 kg of kaolin, and 2 kg of sesbania powder were mixed evenly, and put into a powerful ball-rolling machine to carry out the stirring while an appropriate amount of deionized water was sprayed so that the solid powder was aggregated into small balls. The amount of water sprayed when rolling the balls was 10% by mass of the solid powder. After screening, small balls with a particle size of 500-800 microns were taken, dried at 90 °C for 5 hours, and calcined at 550 °C for 3 hours.

(2) In-situ crystallization: 65 kg of the calcined small balls from the step of ball-rolling and shaping were placed in 210 liters of a sodium hydroxide hydroxide. The concentration of hydroxide ions in the solution was 0.4 mol/L. The in-situ crystallization treatment was performed at 90 °C for 3 hours, the in-situ crystallized small balls were water-washed until the pH of the washing solution was less than 10, and dried at 90 °C for 3 hours to obtain small balls as matrix.

(3) Ion exchange: 600 mL of in-situ crystallized and dried small balls as matrix were loaded into an ion-exchange column for cation exchange, and the exchange was continuously performed with 0.40 M strontium chloride solution at a volume space velocity of 5.0 $h^{-1}$ at 96 °C under 0.1 MPa for 8 hours, and the total amount of the used strontium chloride solution was 24 L. After the ion exchange was completed, the solid was washed with 6 L of deionized water at 80 °C, dried under a nitrogen atmosphere at 70 °C for 16 hours, and activated at 180 °C for 3 hours in a nitrogen atmosphere to produce an adsorbent I.

The water mass fraction, toluene adsorption capacity, liquid phase static adsorption capacity, crushing rate, and bulk density of the prepared adsorbent I are shown in Table 4.

TABLE 4

| Example No. | Water mass fraction, % | Toluene adsorption capacity, mg/g | Liquid phase static adsorption capacity, mg/g | Crushing rate (130N), % | Bulk density, g/cm$^3$ |
|---|---|---|---|---|---|
| Example 1 | 5.48 | 188 | 155 | 0.5 | 0.76 |
| Comparative Example 3 | 5.05 | 20 | 10 | 0.6 | 0.66 |

As can be seen from Table 4, in Comparative Example 3, the adsorbent prepared by using the A-type molecular sieve almost had zero adsorption capacity for aromatic hydrocarbons, a reduced bulk density and an increased crushing rate, reducing the raw material processing capacity of the processing apparatus and reducing the strength of the adsorbent, which further affected the yield of the target product and could not produce products with qualified purity. At the same time, the reduction in the strength of the adsorbent in the form of small balls would aggravate the pressure drop in the adsorption column and shorten the service life of the adsorbent.

Example 7

In order to evaluate the adsorption selectivity of the highly selective adsorbent of the present invention, a dynamic pulse experimental device was used to measure its adsorption selectivity and the adsorption and desorption rates of the separated target product. The device consisted of a feed system, an adsorption column, a heating furnace, a pressure control valve and the like. The adsorption column was a Φ8×900 mm stainless steel tube. The lower inlet of the adsorption column was connected to a feed and a nitrogen system, and the upper outlet was connected to a pressure control valve and then connected to an effluent collector.

The method for measuring the adsorption selectivity of the adsorbent was as follows: the weighed adsorbent particles to be measured were put into the adsorption column and thoroughly shaked, and the gas in the system was removed in a nitrogen atmosphere. The system pressure was increased to 0.85 MPa, and the temperature was increased to 145 °C. After introducing the desorbent was stopped, 5 mL to 10 mL of a pulse feed solution was injected into the system at a liquid flow rate of 1.5 mL/h. This feed solution contained a tracer that was not adsorbed. Subsequently, the desorbent was introduced at the same volume space velocity for desorption. For every other 2 mL, 3 drops of the desorption solution samples were taken and analyzed by gas chromatography. The volume of the desorbent used for desorption was taken as the abscissa and the concentration of each component of the pulse feed solution was taken as the ordinate, the desorption curve for each element of the pulse feed solution was plotted, as shown in FIG. 1. Among them, the non-adsorbed tracer could be used to obtain the dead volume of the adsorption system. The midpoint of the half-peak width of the tracer was taken as the zero point, and the net retention volume from the midpoint of the half-peak width of each component to the zero point was measured. The net retention volume of any component was proportional to the distribution coefficient at adsorption equilibrium, reflecting the acting force between each component and the adsorbent material. The ratio of the net retention volumes of the two components was the separation coefficient β. For example, the ratio of the net retention volume of 1,2,3-trimethylbenzene to the net retention volume of indan was the adsorbability ratio of the adsorbent material for the two, i.e. the separation coefficient of 1,2,3-trimethylbenzene relative to indan, noted as $\beta_{1,2,3\text{-}trimethylbenzene/indan}$. The separation degree could usually also be used as one of the indicators of the separation efficiency of an adsorbent, especially when evaluating the adsorption and separation performance of different adsorbents under the same operating parameters. The separation degree was equal to the ratio of the difference between the net retention volumes of adjacent pulse peaks to the average value of the half-peak widths of the two pulse peaks. For example, the ratio of the difference between the net retention volume of 1,2,3-trimethylbenzene and the net retention volume of indan to the average value of the half-peak widths of the pulse peaks of the two is the separation degree between the two peaks, noted as $R_{1,2,3\text{-}trimethylbenzene/indan}$.

26 mL of the highly selective adsorbent A prepared in Example 1 was taken for a liquid phase pulse experiment to measure its adsorption selectivity and separation degree, and the adsorption and desorption rates of 4-ethyltoluene. The desorbent used in the experiment was 50 wt % toluene and 50 wt % n-heptane. The composition of the pulse feed solution was each 2 wt % of three methylethylbenzene isomers, three trimethylbenzene isomers, three methylpropylbenzene isomers, propylbenzene, para-diethylbenzene, indane, 2-ethyl-paraxylene, 4-ethyl-metaxylene, and n-nonane (NC9) and 70 wt % of desorbent, wherein n-nonane was the tracer. The obtained desorption curve was shown in FIG. 1. The results for separation coefficient and separation degree between each of 1,3,5-trimethylbenzene, 1,2,4-trimethylbenzene, and 1,2,3-trimethylbenzene and other components are shown in Table 5.

TABLE 5

| $R_{1,2,3\text{-}trimethylbenzene/i}$ | $\beta_{1,2,3\text{-}trimethylbenzene/i}$ | $R_{1,2,4\text{-}trimethylbenzene/i}$ | $\beta_{1,2,4\text{-}trimethylbenzene/i}$ | $R_{1,3,5\text{-}trimethylbenzene/i}$ | $\beta_{1,3,5\text{-}trimethylbenzene/i}$ | i |
|---|---|---|---|---|---|---|
| 1.46 | 6.03 | 1.5 | 4.83 | 1.25 | 6.74 | propylbenzene |
| 1.23 | 3.71 | 0.96 | 2.97 | 1.09 | 4.15 | 4-ethyltoluene |
| 1.26 | 4.00 | 0.99 | 3.21 | 1.11 | 4.48 | 3-ethyltoluene |
| 1.07 | 2.16 | 0.78 | 2.16 | 0.96 | 3.01 | 2-ethyltoluene |
| 1.39 | 5.47 | 1.13 | 4.38 | 1.21 | 6.12 | 3-propyltoluene |
| 1.3 | 4.69 | 1.04 | 3.76 | 1.14 | 5.25 | 4-propyltoluene |
| 1.56 | 7.98 | 1.30 | 6.40 | 1.33 | 8.93 | 1,4-diethylbenzene |
| 1.09 | 3.18 | 0.83 | 2.55 | 0.99 | 3.55 | 2-propyltoluene |
| 0.95 | 2.37 | 0.67 | 1.90 | 0.88 | 2.65 | 2-ethyl-paraxylene |
| 0.86 | 1.98 | 0.55 | 1.59 | 0.8 | 2.21 | 4-ethyl-metaxylene |
| 0.96 | 2.20 | 0.66 | 1.77 | 0.88 | 2.47 | indan |

Example 8

The separation of trimethylbenzenes from a heavy aromatic hydrocarbon was performed according to the method of Example 7, except that the adsorbent was the adsorbent B. The results for separation coefficient and separation degree between each of 1,3,5-trimethylbenzene, 1,2,4-trimethylbenzene, and 1,2,3-trimethylbenzene and other components are shown in Table 6.

TABLE 6

| $R_{1,2,3\text{-}trimethylbenzene/i}$ | $\beta_{1,2,3\text{-}trimethylbenzene/i}$ | $R_{1,2,4\text{-}trimethylbenzene/i}$ | $\beta_{1,2,4\text{-}trimethylbenzene/i}$ | $R_{1,3,5\text{-}trimethylbenzene/i}$ | $\beta_{1,3,5\text{-}trimethylbenzene/i}$ | i |
|---|---|---|---|---|---|---|
| 1.33 | 3.82 | 0.83 | 2.33 | 0.87 | 2.50 | propylbenzene |
| 1.06 | 2.15 | 0.59 | 1.32 | 0.60 | 1.41 | 4-ethyltoluene |
| 1.11 | 2.48 | 0.61 | 1.51 | 0.68 | 1.62 | 3-ethyltoluene |
| 0.86 | 1.85 | 0.50 | 1.23 | 0.56 | 1.21 | 2-ethyltoluene |

TABLE 6-continued

| $R_{1,2,3\text{-trimethylbenzene}/i}$ | $\beta_{1,2,3\text{-trimethylbenzene}/i}$ | $R_{1,2,4\text{-trimethylbenzene}/i}$ | $\beta_{1,2,4\text{-trimethylbenzene}/i}$ | $R_{1,3,5\text{-trimethylbenzene}/i}$ | $\beta_{1,3,5\text{-trimethylbenzene}/i}$ | i |
|---|---|---|---|---|---|---|
| 2.93 | 4.96 | 1.64 | 2.89 | 1.70 | 3.01 | 3-propyltoluene |
| 2.80 | 4.19 | 1.42 | 2.55 | 1.55 | 2.63 | 4-propyltoluene |
| 2.18 | 2.45 | 1.13 | 1.82 | 1.25 | 1.85 | 1,4-diethylbenzene |
| 2.88 | 4.32 | 1.50 | 2.74 | 1.64 | 2.85 | 2-propyltoluene |
| 1.51 | 1.69 | 0.79 | 1.25 | 0.88 | 1.28 | 2-ethyl-paraxylene |
| 1.64 | 1.81 | 0.80 | 1.45 | 0.94 | 1.40 | 4-ethyl-metaxylene |
| 0.68 | 1.61 | 0.66 | 1.25 | 0.88 | 1.25 | indan |

Example 9

The separation of trimethylbenzenes from a heavy aromatic hydrocarbon was performed according to the method of Example 7, except that the adsorbent was the adsorbent C. The results for separation coefficient and separation degree between each of 1,3,5-trimethylbenzene, 1,2,4-trimethylbenzene, and 1,2,3-trimethylbenzene and other components are shown in Table 7.

TABLE 7

| $R_{1,2,3\text{-trimethylbenzene}/i}$ | $\beta_{1,2,3\text{-trimethylbenzene}/i}$ | $R_{1,2,4\text{-trimethylbenzene}/i}$ | $\beta_{1,2,4\text{-trimethylbenzene}/i}$ | $R_{1,3,5\text{-trimethylbenzene}/i}$ | $\beta_{1,3,5\text{-trimethylbenzene}/i}$ | i |
|---|---|---|---|---|---|---|
| 3.04 | 9.21 | 1.54 | 3.81 | 1.48 | 3.80 | propylbenzene |
| 2.96 | 6.99 | 1.39 | 2.89 | 1.33 | 2.89 | 4-ethyltoluene |
| 2.69 | 5.27 | 1.09 | 2.18 | 1.04 | 2.18 | 3-ethyltoluene |
| 2.41 | 3.32 | 0.58 | 1.37 | 0.55 | 1.37 | 2-ethyltoluene |
| 7.54 | 6.29 | 1.29 | 2.74 | 1.30 | 2.75 | 3-propyltoluene |
| 8.14 | 10.87 | 2.53 | 4.12 | 2.55 | 4.15 | 4-propyltoluene |
| 8.24 | 12.38 | 2.72 | 5.68 | 2.72 | 5.70 | 1,4-diethylbenzene |
| 8.01 | 9.86 | 2.44 | 4.00 | 2.44 | 4.05 | 2-propyltoluene |
| 6.50 | 3.63 | 1.55 | 1.45 | 1.56 | 1.45 | 2-ethyl-paraxylene |
| 6.46 | 3.58 | 1.50 | 1.41 | 1.50 | 1.42 | 4-ethyl-metaxylene |
| 2.18 | 2.84 | 0.50 | 1.27 | 0.59 | 1.37 | indan |

Example 10

The separation of trimethylbenzenes from a heavy aromatic hydrocarbon was performed according to the method of Example 7, except that the adsorbent was the adsorbent D. The results for separation coefficient and separation degree between each of 1,3,5-trimethylbenzene, 1,2,4-trimethylbenzene, and 1,2,3-trimethylbenzene and other components are shown in Table 8.

TABLE 8

| $R_{1,2,3\text{-trimethylbenzene}/i}$ | $\beta_{1,2,3\text{-trimethylbenzene}/i}$ | $R_{1,2,4\text{-trimethylbenzene}/i}$ | $\beta_{1,2,4\text{-trimethylbenzene}/i}$ | $R_{1,3,5\text{-trimethylbenzene}/i}$ | $\beta_{1,3,5\text{-trimethylbenzene}/i}$ | i |
|---|---|---|---|---|---|---|
| 2.41 | 8.32 | 1.23 | 3.68 | 1.27 | 4.38 | propylbenzene |
| 2.36 | 5.43 | 1.24 | 2.40 | 1.14 | 2.85 | 4-ethyltoluene |
| 2.22 | 4.33 | 0.87 | 1.92 | 0.98 | 2.28 | 3-ethyltoluene |
| 2.03 | 3.40 | 0.60 | 1.50 | 0.77 | 1.79 | 2-ethyltoluene |
| 5.24 | 4.96 | 1.13 | 2.63 | 2.44 | 2.74 | 3-propyltoluene |
| 7.81 | 9.32 | 1.90 | 2.95 | 2.05 | 3.05 | 4-propyltoluene |
| 7.86 | 9.82 | 2.01 | 2.98 | 2.56 | 3.15 | 1,4-diethylbenzene |
| 5.04 | 4.88 | 1.20 | 2.75 | 2.59 | 2.88 | 2-propyltoluene |
| 6.21 | 3.44 | 1.07 | 1.88 | 0.78 | 2.38 | 2-ethyl-paraxylene |
| 6.25 | 3.50 | 1.15 | 1.99 | 1.08 | 2.72 | 4-ethyl-metaxylene |
| 1.57 | 2.46 | 0.63 | 1.35 | 0.86 | 1.49 | indan |

Example 11

The separation of trimethylbenzenes from a heavy aromatic hydrocarbon was performed according to the method of Example 7, except that the adsorbent was the adsorbent E. The results for separation coefficient and separation degree between each of 1,3,5-trimethylbenzene, 1,2,4-trimethylbenzene, and 1,2,3-trimethylbenzene and other components are shown in Table 9.

TABLE 9

| $R_{1,2,3\text{-}trimethylbenzene/i}$ | $\beta_{1,2,3\text{-}trimethylbenzene/i}$ | $R_{1,2,4\text{-}trimethylbenzene/i}$ | $\beta_{1,2,4\text{-}trimethylbenzene/i}$ | $R_{1,3,5\text{-}trimethylbenzene/i}$ | $\beta_{1,3,5\text{-}trimethylbenzene/i}$ | i |
|---|---|---|---|---|---|---|
| 1.22 | 5.33 | 1.25 | 4.03 | 1.04 | 5.62 | propylbenzene |
| 1.46 | 3.19 | 0.80 | 2.48 | 0.91 | 3.46 | 4-ethyltoluene |
| 1.55 | 3.63 | 0.83 | 2.68 | 0.93 | 3.73 | 3-ethyltoluene |
| 0.78 | 1.80 | 0.65 | 1.65 | 0.80 | 2.11 | 2-ethyltoluene |
| 1.98 | 4.86 | 0.94 | 3.65 | 1.01 | 5.10 | 3-propyltoluene |
| 1.58 | 4.01 | 0.87 | 3.13 | 0.95 | 4.38 | 4-propyltoluene |
| 2.55 | 6.95 | 1.08 | 5.33 | 1.11 | 7.44 | 1,4-diethylbenzene |
| 1.05 | 2.85 | 0.69 | 2.13 | 0.83 | 2.96 | 2-propyltoluene |
| 0.85 | 2.08 | 0.56 | 1.58 | 0.73 | 2.21 | 2-ethyl-paraxylene |
| 0.78 | 1.85 | 0.50 | 1.33 | 0.67 | 1.84 | 4-ethyl-metaxylene |
| 0.80 | 1.93 | 0.55 | 1.38 | 0.70 | 1.86 | indan |

Comparative Example 4

The separation of trimethylbenzenes from a heavy aromatic hydrocarbon was performed according to the method of Example 7, except that the adsorbent was the adsorbent F. The results for separation coefficient and separation degree between each of 1,3,5-trimethylbenzene, 1,2,4-trimethylbenzene, and 1,2,3-trimethylbenzene and other components are shown in Table 10.

TABLE 10

| $R_{1,2,3\text{-}trimethylbenzene/i}$ | $\beta_{1,2,3\text{-}trimethylbenzene/i}$ | $R_{1,2,4\text{-}trimethylbenzene/i}$ | $\beta_{1,2,4\text{-}trimethylbenzene/i}$ | $R_{1,3,5\text{-}trimethylbenzene/i}$ | $\beta_{1,3,5\text{-}trimethylbenzene/i}$ | i |
|---|---|---|---|---|---|---|
| 0.53 | 1.59 | 0.44 | 1.50 | −0.40 | 0.57 | propylbenzene |
| −0.69 | 0.62 | −0.77 | 0.58 | −1.45 | 0.22 | 4-ethyltoluene |
| 0.82 | 2.42 | 0.72 | 2.27 | −0.08 | 0.87 | 3-ethyltoluene |
| 0.29 | 1.25 | 0.20 | 1.17 | −0.66 | 0.45 | 2-ethyltoluene |
| 1.63 | 3.47 | 1.60 | 3.25 | 0.35 | 1.22 | 3-propyltoluene |
| 0.40 | 1.21 | 0.35 | 1.10 | −0.98 | 0.40 | 4-propyltoluene |
| −0.86 | 0.73 | −0.95 | 0.56 | −1.55 | 0.11 | 1,4-diethylbenzene |
| 1.05 | 2.37 | 0.80 | 2.00 | 0.22 | 1.02 | 2-propyltoluene |
| 0.73 | 1.47 | 0.55 | 1.15 | −0.81 | 0.55 | 2-ethyl-paraxylene |
| 0.11 | 1.05 | −0.11 | 0.91 | −1.00 | 0.35 | 4-ethyl-metaxylene |
| −0.04 | 0.97 | −0.12 | 0.94 | −0.96 | 0.35 | indan |

Example 12

A small simulated moving bed apparatus was used to carry out the liquid phase adsorption separation of a heavy aromatic hydrocarbon to separate the trimethylbenzene isomers therein. The device was composed of 24 columns connected in series. As an adsorption bed, the cavity inside the column used to accommodate the selective adsorbent of the present invention was 200 mm high and 40 mm in diameter. The 24th column was connected to the first column through a pump so that the fluid in the column was circulated, and materials could be introduced or extracted from the joints of the columns. 7 columns were between the raffinate outlet and the raw material inlet and used as the adsorption zone; 9 columns were between the raw material inlet and the extract outlet and used as the purification zone; 5 columns were between the extract outlet and the desorbent inlet and used as the desorption zone; and 3 columns were between the desorbent inlet and the raffinate outlet and used as the isolation zone. The positions of the inlet and outlet of a material were changed according to the step time, and every other step time, the inlet and outlet were moved forward by one column. As shown in FIG. 2, the inlet and outlet were moved from the position of the solid arrow to the position of the dotted arrow. At the next step time, the moving was advanced in the predetermined direction and so on. The positions of the inlet and outlet were changed in sequence until they returned to their starting positions, which is one cycle. One step time was 80 seconds, and one cycle was 32 minutes.

The adsorption raw material was a reformed heavy aromatic hydrocarbon. The temperature of the adsorption raw material entering the adsorption bed was controlled to 160 °C and the operating pressure was 0.88 MPa. A total of 2400 g of adsorbent A was loaded, the desorbent was 99.9 wt % toluene, the raw material feed rate was 0.50 kg/h, the desorbent injection rate was 1.52 kg/h, the withdrawing rate of the extract was 0.70 kg/h, and the withdrawing rate of the raffinate was 1.32 kg/h, the mass flow ratio of the desorbent entering the simulated moving bed and the heavy aromatic hydrocarbon raw material was 3.04, and the flow rate of the heavy aromatic hydrocarbon raw material per unit mass of adsorbent was 0.21 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$\text{Trimethylbenzene (TMB) purity} = \frac{X_{1,3,5\text{-}TMB} + X_{1,3,4\text{-}TMB} + X_{1,2,3\text{-}TMB}}{X_{all\ heavy\ aromatic\ components}} \times 100\%$$

wherein X is the mass fraction of each component in the extract;

$$TMB\ \text{yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 90.97% and 99.21 wt % respectively.

Example 13

Trimethylbenzenes were separated from a heavy aromatic hydrocarbon according to the method of Example 12. The adsorption raw material was a reformed heavy aromatic hydrocarbon. The temperature of the adsorption raw material entering the adsorption bed was controlled to 160 °C and the operating pressure was 0.88 MPa. A total of 1950 g of adsorbent B was loaded, the desorbent was 99.9 wt % toluene, the raw material feed rate was 0.45 kg/h, the desorbent injection rate was 1.57 kg/h, the withdrawing rate of the extract was 0.75 kg/h, and the withdrawing rate of the raffinate was 1.27 kg/h, the mass flow ratio of the desorbent entering the simulated moving bed and the heavy aromatic hydrocarbon raw material was 3.49, and the flow rate of the heavy aromatic hydrocarbon raw material per unit mass of adsorbent was 0.23 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$\text{Trimethylbenzene(TMB) purity} = \frac{X_{1,3,5\text{-}TMB} + X_{1,3,4\text{-}TMB} + X_{1,2,3\text{-}TMB}}{X_{all\ heavy\ aromatic\ components}} \times 100\%$$

wherein X is the mass fraction of each component in the extract;

$$TMB\ \text{yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 86.31% and 99.08 wt % respectively.

Example 14

Trimethylbenzenes were separated from a heavy aromatic hydrocarbon according to the method of Example 12. The adsorption raw material was a reformed heavy aromatic hydrocarbon. The temperature of the adsorption raw material entering the adsorption bed was controlled to 160 °C and the operating pressure was 0.88 MPa.

A total of 2250 g of adsorbent D was loaded, the desorbent was 99.9 wt % toluene, the raw material feed rate was 0.50 kg/h, the desorbent injection rate was 1.68 kg/h, the withdrawing rate of the extract was 0.72 kg/h, and the withdrawing rate of the raffinate was 1.46 kg/h, the mass flow ratio of the desorbent entering the simulated moving bed and the heavy aromatic hydrocarbon raw material was 3.36, and the flow rate of the heavy aromatic hydrocarbon raw material per unit mass of adsorbent was 0.22 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$\text{Trimethylbenzene(TMB) purity} = \frac{X_{1,3,5\text{-}TMB} + X_{1,3,4\text{-}TMB} + X_{1,2,3\text{-}TMB}}{X_{all\ heavy\ aromatic\ components}} \times 100\%$$

wherein X is the mass fraction of each component in the extract;

$$TMB\ \text{yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 88.11% and 99.15 wt % respectively.

Example 15

Trimethylbenzenes were separated from a heavy aromatic hydrocarbon according to the method of Example 12. The adsorption raw material was a reformed heavy aromatic hydrocarbon. The temperature of the adsorption raw material entering the adsorption bed was controlled to 160 °C and the operating pressure was 0.88 MPa. A total of 2350 g of adsorbent G was loaded, the desorbent was 99.9 wt % toluene, the raw material feed rate was 0.50 kg/h, the desorbent injection rate was 1.68 kg/h, the withdrawing rate of the extract was 0.72 kg/h, and the withdrawing rate of the raffinate was 1.46 kg/h, the mass flow ratio of the desorbent entering the simulated moving bed and the heavy aromatic hydrocarbon raw material was 3.36, and the flow rate of the heavy aromatic hydrocarbon raw material per unit mass of adsorbent was 0.21 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$Trimethylbenzene(TMB)\text{ purity} = \frac{X_{1,3,5-TMB} + X_{1,3,4-TMB} + X_{1,2,3-TMB}}{X_{all\ heavy\ aromatic\ components}} \times 100\%$$

wherein X is the mass fraction of each component in the extract;

$$TMB\text{ yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 89.00% and 99.15 wt % respectively.

Example 16

Trimethylbenzenes were separated from a heavy aromatic hydrocarbon according to the method of Example 12. The adsorption raw material was a reformed heavy aromatic hydrocarbon. The temperature of the adsorption raw material entering the adsorption bed was controlled to 160 °C and the operating pressure was 0.88 MPa.

A total of 2000 g of adsorbent E was loaded, the desorbent was 99.9 wt % toluene, the raw material feed rate was 0.55 kg/h, the desorbent injection rate was 1.52 kg/h, the withdrawing rate of the extract was 0.70 kg/h, and the withdrawing rate of the raffinate was 1.32 kg/h, the mass flow ratio of the desorbent entering the simulated moving bed and the heavy aromatic hydrocarbon raw material was 2.76, and the flow rate of the heavy aromatic hydrocarbon raw material per unit mass of adsorbent was 0.28 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$Trimethylbenzene(TMB)\text{ purity} = \frac{X_{1,3,5-TMB} + X_{1,3,4-TMB} + X_{1,2,3-TMB}}{X_{all\ heavy\ aromatic\ components}} \times 100\%$$

wherein X is the mass fraction of each component in the extract;

$$TMB\text{ yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 90.90% and 99.15 wt % respectively.

Comparative Example 5

Trimethylbenzenes were separated from a heavy aromatic hydrocarbon according to the method of Example 12. The adsorption raw material was a reformed heavy aromatic hydrocarbon. The temperature of the adsorption raw material entering the adsorption bed was controlled to 160 °C and the operating pressure was 0.88 MPa.

A total of 2890 g of adsorbent F was loaded, the desorbent was 99.9 wt % toluene, the raw material feed rate was 0.40 kg/h, the desorbent injection rate was 1.88 kg/h, the withdrawing rate of the extract was 0.85 kg/h, and the withdrawing rate of the raffinate was 1.43 kg/h, the mass flow ratio of the desorbent entering the simulated moving bed and the heavy aromatic hydrocarbon raw material was 4.70, and the flow rate of the heavy aromatic hydrocarbon raw material per unit mass of adsorbent was 0.14 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$Trimethylbenzene(TMB)\text{ purity} = \frac{X_{1,3,5-TMB} + X_{1,3,4-TMB} + X_{1,2,3-TMB}}{X_{all\ heavy\ aromatic\ components}} \times 100\%$$

wherein X is the mass fraction of each component in the extract;

$$TMB\text{ yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 50.31% and 48.08 wt % respectively.

Comparative Example 6

Trimethylbenzenes were separated from a heavy aromatic hydrocarbon according to the method of Example 12. The adsorption raw material was a reformed heavy aromatic hydrocarbon. The temperature of the adsorption raw material entering the adsorption bed was controlled to 160 °C and the operating pressure was 0.88 MPa.

A total of 2280 g of adsorbent H was loaded, the desorbent was 99.9 wt % toluene, the raw material feed rate was 0.50 kg/h, the desorbent injection rate was 1.52 kg/h, the withdrawing rate of the extract was 0.70 kg/h, and the withdrawing rate of the raffinate was 1.32 kg/h, the mass flow ratio of the desorbent entering the simulated moving bed and the heavy aromatic hydrocarbon raw material was 3.04, and the flow rate of the heavy aromatic hydrocarbon raw material per unit mass of adsorbent was 0.22 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$\text{Trimethylbenzene}(TMB)\text{ purity} = \frac{X_{1,3,5-TMB} + X_{1,3,4-TMB} + X_{1,2,3-TMB}}{X_{\text{all heavy aromatic components}}} \times 100\%$$

wherein X is the mass fraction of each component in the extract;

$$TMB\text{ yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 80.92% and 97.42 wt % respectively.

Comparative Example 7

Trimethylbenzenes were separated from a heavy aromatic hydrocarbon according to the method of Example 12. The adsorption raw material was a reformed heavy aromatic hydrocarbon. The temperature of the adsorption raw material entering the adsorption bed was controlled to 160 °C and the operating pressure was 0.88 MPa.

A total of 1900 g of adsorbent I was loaded, the desorbent was 99.9 wt % toluene, the raw material feed rate was 0.50 kg/h, the desorbent injection rate was 1.52 kg/h, the withdrawing rate of the extract was 0.70 kg/h, and the withdrawing rate of the raffinate was 1.32 kg/h, the mass flow ratio of the desorbent entering the simulated moving bed and the heavy aromatic hydrocarbon raw material was 3.04, and the flow rate of the heavy aromatic hydrocarbon raw material per unit mass of adsorbent was 0.26 kg/(h·kg adsorbent).

After the simulated moving bed was running stably, a mixed sample of the extract and the raffinate for one cycle was taken and analyzed for its composition. According to the analysis results, the calculation method for the purity and yield of the trimethylbenzene mixture was:

$$\text{Trimethylbenzene}(TMB)\text{ purity} = \frac{X_{1,3,5-TMB} + X_{1,3,4-TMB} + X_{1,2,3-TMB}}{X_{\text{all heavy aromatic components}}} \times 100\%$$

wherein X is the mass fraction of each component in the extract;

$$TMB\text{ yield} = \frac{X_{TMB,extract} \times Q_{extract}}{X_{TMB,extract} \times Q_{extract} + X_{TMB,raffinate} \times Q_{raffinate}} \times 100\%$$

wherein $X_{TMB,\ extract}$ is the sum of the mass fractions of three trimethylbenzenes in the extract, $Q_{extract}$ is the mass flow rate of the extract, wherein $X_{TMB,\ raffinate}$ is the sum of the mass fractions of three trimethylbenzenes in the raffinate, $Q_{raffinate}$ is the mass flow rate of the raffinate.

The yield and purity of three trimethylbenzenes obtained as the target product were 10.22% and 10.11 wt % respectively.

Example 17

As shown in FIG. 3, three trimethylbenzene monomers were obtained respectively with an apparatus using a combined adsorption separation and distillation process. The feed rate of the heavy aromatic hydrocarbon was 20 t/h. The temperature of the adsorption separation unit was 160 °C, the pressure was 0.8 MPa, and the desorbent was toluene, and the loaded adsorbent was adsorbent A. The distillation unit was a dividing wall column. The temperature at the top of the column was 165 °C. 1,3,5-trimethylbenzene was produced from the top of the column. The side-line temperature was 173 °C. 1,2,4-trimethylbenzene was produced from the side-line. 1,2,3-trimethylbenzene was produced at the bottom of the column. All pressures in the dividing wall column were 0.1 MPa. The purity and yield of 1,3,5-trimethylbenzene, 1,2,4-trimethylbenzene, and 1,2,3-trimethylbenzene are shown in Table 11.

TABLE 11

| | Mononers | | |
|---|---|---|---|
| Properties | 1,3,5-TMB | 1,3,4-TMB | 1,2,3-TMB |
| Purity | 99.0% | 99.8% | 97.2% |
| Yield | 86% | 90% | 94% |

Example 18

The separation of trimethylbenzenes from a heavy aromatic hydrocarbon was performed according to the method of Example 17. Three trimethylbenzene monomers were obtained respectively with an apparatus using a combined adsorption separation and distillation process. The feed rate of the heavy aromatic hydrocarbon was 20 t/h. The temperature of the adsorption separation unit was 162 °C, the pressure was 0.8 MPa, and the desorbent was toluene, and the loaded adsorbent was adsorbent B. The distillation unit was a dividing wall column. The temperature at the top of the column was 165 °C. 1,3,5-trimethylbenzene was produced from the top of the column. The side-line temperature was 175 °C. 1,2,4-trimethylbenzene was produced from the side-line. 1,2,3-trimethylbenzene was produced at the bottom of the column. All pressures in the dividing wall column were 0.1 MPa. The purity and yield of 1,3,5-trimethylbenzene, 1,2,4-trimethylbenzene, and 1,2,3-trimethylbenzene are shown in Table 12.

TABLE 12

| | Mononers | | |
|---|---|---|---|
| Properties | 1,3,5-TMB | 1,3,4-TMB | 1,2,3-TMB |
| Purity | 98.5% | 99.3% | 97.0% |
| Yield | 84% | 86% | 92% |

Example 19

The separation of trimethylbenzenes from a heavy aromatic hydrocarbon was performed according to the method of Example 17. Three trimethylbenzene monomers were obtained respectively with an apparatus using a combined adsorption separation and distillation process. The feed rate of the heavy aromatic hydrocarbon was 20 t/h. The temperature of the adsorption separation unit was 165 °C, the pressure was 0.8 MPa, and the desorbent was toluene, and the loaded adsorbent was adsorbent D. The distillation unit was a dividing wall column. The temperature at the top of the column was 165 °C. 1,3,5-trimethylbenzene was produced from the top of the column. The side-line temperature was 175 °C. 1,2,4-trimethylbenzene was produced from the side-line. 1,2,3-trimethylbenzene was produced at the bottom of the column. All pressures in the dividing wall column were 0.1 MPa. The purity and yield of 1,3,5-trimethylbenzene, 1,2,4-trimethylbenzene, and 1,2,3-trimethylbenzene are shown in Table 13.

TABLE 13

| | Mononers | | |
|---|---|---|---|
| Properties | 1,3,5-TMB | 1,3,4-TMB | 1,2,3-TMB |
| Purity | 98.6% | 99.4% | 97.1% |
| Yield | 85% | 87% | 93% |

Comparative Example 8

The separation of trimethylbenzenes from a heavy aromatic hydrocarbon was performed according to the method of Example 17. Three trimethylbenzene monomers were obtained respectively with an apparatus using a combined adsorption separation and distillation process. The feed rate of the heavy aromatic hydrocarbon was 20 t/h. The temperature of the adsorption separation unit was 165 °C, the pressure was 0.8 MPa, and the desorbent was toluene, and the loaded adsorbent was adsorbent F. The distillation unit was a dividing wall column. The temperature at the top of the column was 165 °C. 1,3,5-trimethylbenzene was produced from the top of the column. The side-line temperature was 175 °C. 1,2,4-trimethylbenzene was produced from the side-line. 1,2,3-trimethylbenzene was produced at the bottom of the column. All pressures in the dividing wall column were 0.1 MPa. The purity and yield of 1,3,5-trimethylbenzene, 1,2,4-trimethylbenzene, and 1,2,3-trimethylbenzene are shown in Table 14.

TABLE 14

| | Mononers | | |
|---|---|---|---|
| Properties | 1,3,5-TMB | 1,3,4-TMB | 1,2,3-TMB |
| Purity | 7.5% | 28.5% | 9.3% |

Comparative Example 9

Three trimethylbenzene monomers were obtained respectively with a distillation apparatus. The feed rate of the heavy aromatic hydrocarbon was 20 t/h. The heavy aromatic hydrocarbon raw material was pre-treated to remove C8s and then sent to a first distillation column. 1,3,5-trimethylbenzene was produced from the top of the first distillation column. The bottom material of the first distillation column was sent to a second distillation column. 1,2,4-trimethylbenzene was produced from the top of the second distillation column and 1,2,3-trimethylbenzene was produced from the bottom of the second distillation column. The first distillation column had a column top temperature of 166 °C and a plate number of 100. The second distillation column had a column top temperature of 170 °C and a plate number of 90. All pressures in the distillation columns were 0.1 MPa. The purity of 1,3,5-trimethylbenzene, 1,2,4-trimethylbenzene, and 1,2,3-trimethylbenzene are shown in Table 15.

TABLE 15

| | Mononers | | |
|---|---|---|---|
| Properties | 1,3,5-TMB | 1,3,4-TMB | 1,2,3-TMB |
| Purity | 29.5% | 98.1% | 59.6% |

It can be seen from Table 14 and Table 15 that conventional distillation processes and adsorbents outside the scope of the present invention cannot obtain three trimethylbenzene monomers with high-purity, and cannot meet the requirements for subsequent further utilization. With the combined process of adsorption separation and distillation, special adsorbents that preferentially adsorb trimethylbenzenes are used to obtain 1,3,5-trimethylbenzene, 1,2,4-trimethylbenzene, and 1,2,3-trimethylbenzene monomers with high purity at high yield. In particular, three trimethylbenzenes are obtained with extremely high purity at extremely high yield. Three trimethylbenzene products with high added value can be obtained with high purity at high yield, which not only reduces the process operation cost and improves the resource utilization rate of heavy aromatic hydrocarbons, but also maximizes the economic added value of the heavy aromatic hydrocarbon products and extends the industrial chain.

INDUSTRIAL APPLICABILITY

The present invention provides an adsorbent for trimethylbenzene-based compounds and preparation method thereof. The adsorbent of the present invention has excellent selectivity for trimethylbenzene-based compounds. The separation method and separation apparatus using the adsorbent of the present invention can produce trimethylbenzene-based compounds and their respective monomers with high purity at high yield.

The invention claimed is:

1. A method for separating trimethylbenzene-based compounds, which comprises the following steps:

an adsorption separation comprising contacting a heavy aromatic hydrocarbon raw material containing trimethylbenzene-based compounds with an adsorbent to adsorb trimethylbenzene-based compounds, and then performing the separation to produce trimethylbenzene-based compounds; and an isomerization step carried out after the adsorption separation to isomerize one or more trimethylbenzene-based compounds, and returning the isomerized stream of trimethylbenzenes having a thermodynamic equilibrium concentration to the adsorption separation step, wherein the adsorbent comprises comprising 93-99 wt % of an X-type molecular sieve and 1-7 wt % of a matrix, based on a total amount of the X-type molecular sieve and the matrix, wherein the matrix is a substance resulting from crystal transformation through in-situ crystallization of a clay mineral, the adsorbent is modified with at least one bivalent cation selected from $Fe^{2+}$, $Co^{2+}$, $Ni^{2+}$, and $Zn^{2+}$ and optionally modified with at least one monovalent cation selected from $Li^{+}$, $Na^{+}$, $K^{+}$, $Rb^{+}$, and $Cs^{+}$.

2. The separation method according to claim 1, relative to a unit mass of adsorbent, the flow rate of the heavy aromatic hydrocarbon raw material is not less than 0.16 kg/(h·kg adsorbent).

3. The separation method according to claim 1, wherein the step of adsorption separation is carried out in a simulated moving bed apparatus, wherein the simulated moving bed apparatus comprises a plurality of adsorption beds loaded with the adsorbent and each adsorption bed is in a desorption zone, a purification zone, an adsorption zone, or and an isolation zone, the adsorption beds disposed between a desorbent injection port and extract withdrawing port constitute the desorption zone, the adsorption beds disposed between extract withdrawing port and a raw material injection port constitute the purification zone, the adsorption beds disposed between the raw material injection port and a raffinate withdrawing port constitute the adsorption zone, the adsorption beds disposed between the raffinate withdrawing port and the desorbent injection port constitute the isolation zone.

4. The separation method according to claim 3, comprising at least one of following features:

during one step time, the withdrawing and injection order of each material in the material flowing direction of the simulated moving bed is desorbent, extract, raw material and raffinate;

the pressure of the simulated moving bed apparatus is 0.5 MPa-1.2 MPa, the temperature is 120 °C-200 °C;

the ratio of mass flow rates of the desorbent and the heavy aromatic hydrocarbon raw material injected into the simulated moving bed apparatus is not greater than 3.6;

a ratio of adsorption beds in the adsorption zone, the purification zone, the desorption zone, and the isolation zone is 29±10%:37±15%:21±5%:13±4%; and the simulated moving bed apparatus has one cycle period of 18-60 minutes.

5. The separation method according to claim 3, wherein, in the simulated moving bed, each adsorption bed of the simulated moving bed is provided with a grid, which is equipped with material injection and withdrawing pipelines of said bed, two flushing liquor pipelines are set up in parallel with material injection and withdrawing pipelines of each adsorption bed; or each pipeline is provided with an on-off valve, the extract is used as the flushing liquor, the flushing liquor from one flushing liquor pipeline is injected into a bed that is located one bed upstream the raw material injection bed, and the flushing liquor from the other flushing liquor pipeline is injected into a bed that is located 2-4 beds downstream the extract withdrawing position; or the grid of each adsorption bed is equipped with one withdrawing and injection pipeline, and multiple parallel on-off valves are set up on the pipeline to control materials to be withdrawn from and injected into the adsorbent beds; or withdrawing and injection pipelines of each adsorbent bed are provided with 6-7 on-off valves; or each adsorption bed is provided with a pipeline for which the flushing liquor is used as the desorbent, the injection position of which is one bed upstream the extract withdrawing position.

6. The separation method according to claim 1, further comprising:

a distillation step, wherein trimethylbenzene-based compounds obtained from the adsorption separation are subjected to distillation to produce 1,3,5-trimethylbenzene, 1,2,4-trimethylbenzene, and 1,2,3-trimethylbenzene respectively, and 1,3,5-trimethylbenzene, 1,2,4-trimethylbenzene, and 1,2,3-trimethylbenzene obtained from the distillation step have purities of not less than 97.0 wt %, 98.0 wt % and 95.0 wt %, respectively, wherein:

in the distillation step, an extract stream from the adsorption separation step is sent to a dividing wall column, 1,3,5-trimethylbenzene is produced from the top of the dividing wall column, 1,2,4-trimethylbenzene is produced from the side-line of the dividing wall column, 1,2,3-trimethylbenzene is produced from the bottom of the dividing wall column, or in the distillation step, an extract stream from the adsorption separation step is sent to the first distillation column, 1,3,5-trimethylbenzene is produced by separation from the column top of the first distillation column, the bottom product of the first distillation column is sent to a second distillation column, 1,2,4-trimethylbenzene is produced by separation from the column top of the second distillation column, 1,2,3-trimethylbenzene is produced from the column bottom of the second distillation column, or in the distillation step, an extract stream from the adsorption separation step is sent to the first distillation column, 1,3,5-trimethylbenzene is produced by separation from the column top of the first distillation column, the bottom product of the first distillation column is sent to a second distillation column, 1,2,4-trimethylbenzene is produced by separation from the column top of the second distillation column, the bottom product of the second distillation column is sent to a third distillation column, 1,2,3-trimethylbenzene is produced by separation from the column top of the third distillation column, the bottom product is an aromatic solvent oil with high boiling point, or in the distillation step, an extract stream from the adsorption separation step is sent to the first distillation column, 1,3,5-trimethylbenzene is produced by separation from the column top of the first distillation column, the column bottom stream is a mixture of 1,2,4-trimethylbenzene and 1,2,3-trimethylbenzene, 1,2,4-trimethylbenzene and 1,2,3-trimethylbenzene are further separated by using a crystallization process, or in the distillation step, 1,2,3-trimethylbenzene can be separated from an extract stream from the adsorption separation step by using a crystallization process, a mixture stream of the residual 1,2,4-trimethylbenzene and 1,3,5-trimethylbenzene is sent to the first distillation column, 1,3,5-trimethylbenzene is produced by separation from the column top of the first distillation column, the column bottom stream is 1,2,4-trimethylbenzene.

7. The separation method according to claim 1, wherein trimethylbenzene-based compounds obtained from the adsorption separation step have a total purity of not less than 99 wt %.

8. The separation method according to claim 6, wherein the isomerization step is carried out between the adsorption separation and the distillation step, at least one of 1,3,5-trimethylbenzene, 1,2,4-trimethylbenzene, and 1,2,3-trimethylbenzene is subjected to the isomerization step, and, after one trimethylbenzene or a mixture of trimethylbenzenes is isomerized, the obtained mixture stream of trimethylbenzenes having a thermodynamic equilibrium concentration is returned to the adsorption separation step for separation.

9. An apparatus for separating trimethylbenzene-based compounds, comprising the following units:

an adsorption separation unit having the adsorbent, and used to adsorb and separate trimethylbenzene-based compounds from a heavy aromatic hydrocarbon raw material containing trimethylbenzene-based compounds to produce trimethylbenzene-based compounds;

an optional distillation unit, which is connected to the downstream of the adsorption separation unit, receives a stream containing trimethylbenzene-based compounds from the adsorption separation unit, and performs the distillation to produce 1,3,5-trimethylbenzene, 1,2,4-trimethylbenzene, and 1,2,3-trimethylbenzene respectively;

an optional raffinate distillation unit, which is connected to the downstream of the adsorption separation unit, receives a stream containing the heavy aromatic hydrocarbon component in which trimethylbenzene-based compounds have been separated by adsorption from the adsorption separation unit, and in which the distillation is performed, to produce a heavy aromatic hydrocarbon component in which trimethylbenzene-based compounds have been separated by adsorption and a desorbent respectively; and an optional isomerization unit, which is located between the adsorption separation unit and the distillation unit, and used to receive a stream containing trimethylbenzene-based compounds from the adsorption separation unit, and in which the isomerization is performed; or which is connected to the downstream of the distillation unit, used to receive at least one of 1,3,5-trimethylbenzene, 1,2,4-trimethylbenzene, and 1,2,3-trimethylbenzene from the distillation unit, and in which the isomerization is performed.

10. The separation apparatus according to claim 9, wherein the adsorption separation unit adopts a simulated moving bed, and the simulated moving bed comprises multiple adsorption beds with loaded adsorbent, each bed has its material injection and withdrawing pipelines, materials that are withdrawn from and injected into the simulated moving bed apparatus divide adsorption beds therein into desorption zone, purification zone, adsorption zone and isolation zone, the adsorption beds between desorbent injection and extract withdrawing constitute the desorption zone, the adsorption beds between extract withdrawing and raw material injection constitute the purification zone, the adsorption beds between raw material injection and raffinate withdrawing constitute the adsorption zone, the adsorption beds between raffinate withdrawing and desorbent injection constitute the isolation zone.

* * * * *